US009867845B2

(12) United States Patent
Guan et al.

(10) Patent No.: US 9,867,845 B2
(45) Date of Patent: Jan. 16, 2018

(54) VECTORS FOR DELIVERY OF AGENTS ACROSS BIOLOGICAL MEMBRANES

(71) Applicant: The Regents of the University of California, Oakland, CA (US)

(72) Inventors: Zhibin Guan, Irvine, CA (US); Hanxiang Zeng, Media, PA (US); Mark Edward Johnson, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/814,475

(22) Filed: Jul. 30, 2015

(65) Prior Publication Data

US 2016/0030590 A1   Feb. 4, 2016

Related U.S. Application Data

(60) Provisional application No. 62/031,158, filed on Jul. 30, 2014.

(51) Int. Cl.
| | |
|---|---|
| A61K 38/00 | (2006.01) |
| C07K 9/00 | (2006.01) |
| A61K 31/713 | (2006.01) |
| C07K 5/02 | (2006.01) |
| C12N 15/11 | (2006.01) |
| A61K 47/60 | (2017.01) |
| A61K 47/64 | (2017.01) |

(52) U.S. Cl.
CPC ............ *A61K 31/713* (2013.01); *A61K 47/60* (2017.08); *A61K 47/645* (2017.08); *C07K 5/0215* (2013.01); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 4,992,417 A * | 2/1991 | Katsoyannis | .......... | C07K 14/62 514/6.1 |
| 2012/0183578 A1 * | 7/2012 | Sinko | ..................... | A61K 47/34 424/278.1 |
| 2014/0242123 A1 | 8/2014 | Guan et al. | | |
| 2014/0288150 A1 | 9/2014 | Guan et al. | | |

FOREIGN PATENT DOCUMENTS

WO    WO2006/060182 A2 *   6/2006

OTHER PUBLICATIONS

Hamley et al. (Biomacromolecules; ACS Publications, 2014, 15, 1543-1559).*

Wu et al. Polycationic dendrimers interact with RNA molecules: polyamine dendrimers inhibit the catalytic activity of Candida ribozymes, Chem. Commun., 2005, 313-315.*
Castanotto et al., "The promises and pitfalls of RNA interference-based therapeutics", Nature 457:426-433 (2009).
Chen et al., "An RNA interference screen uncovers a new molecule in stemcell self-renewal and long-term regeneration", Nature 485(7396): 104-108.
Crombez et al., "A New Potent Secondary Amphipathic Cell—penetrating Peptide for siRNA Delivery Into Mammalian Cells," Molecular Therapy 17(1):95-103 (2009).
Dafik et al., "Fluorinated Lipid Constructs Permit Facile Passage of Molecular Cargo into Living Cells," JACS 131:12091-12093 (2009).
Davis et al., "Evidence of RNAi in humans from systemically administered siRNA via targeted nanoparticles", Nature 464:1067-1070 (2010).
Dietzl et al., "A genome-wide transgenic RNAi library for conditional gene inactivation in *Drosophila*", Nature 448:151-156 (2007).
Dong et al., "Lipopeptide nanoparticles for potent and selective siRNA delivery in rodents and nonhuman primates", PNAS 111(11):3955-3960 (Mar. 18, 2014).
Fougerolles et al., "Interfering with disease: a progress report on siRNA-based therapeutics", Nat. Rev. Drug Discovery 6:443-410 (2007).
Giljohann et al., "Gene Regulation with Polyvalent siRNA-Nanoparticle Conjugates," JACS 131(6):2072-2073 (2009).
Gilleron et al., "Image-based analysis of lipid nanoparticle—mediated siRNA delivery, intracellular trafficking and endosomal escape" Nature Biotechnology 31:638-646 (2013).
Hafez et al., "On the mechanism whereby cationic lipids promote intracellular delivery of polynucleic acids" Nature 8:1188-1196 (2001).
Hartgerink et al., "Self-Assembly and Mineralization of Peptide-Amphiphile Nanofibers", Science 294:1684-1688 (2010).
Hunter, "Molecular hurdles in polyfectin design and mechanistic background to polycation induced cytotoxicity", Adv. Drug Delivery Rev 58:1523-1531 (2006).
Khalil et al., "Uptake Pathways and Subsequent Intracellular Trafficking in Nonviral Gene Delivery," Pharmacological Reviews 58(1):32-45 (2006).
Kim et al., "In Silico, In Vitro, and In Vivo Studies Indicate the Potential Use of Bolaamphiphiles for Therapeutic siRNAs Delivery", Molecular Therapy—Nucleic Acids 2:e80 (2013).
Kim et al., "Dendronized gold nanoparticles for siRNA delivery" Small 8(21):3253-3256 (2012).
Klein et al., "Nucleic acid transfer with hemifluorinated polycationic lipids" Biomaterials 31:4781-4788 (2010).
Knudsen et aL, "In vivo toxicity of cationic micelles and liposomes" Nanomedicine 11(2):467-477 (Aug. 26, 2014).
Kulkarni et al., "Pendant Polymer:Amino-β-Cyclodextrin:siRNA Guest:Host Nanoparticles as Efficient Vectors for Gene Silencing", JACS 134:7596-7599 (2012).
Kumar et al., "Transvascular delivery of small interfering RNA to the central nervous system", Nature 448:39-43 (2007).

(Continued)

*Primary Examiner* — Jeanette Lieb
(74) *Attorney, Agent, or Firm* — Gavrilovich, Dodd & Lindsey LLP

(57) ABSTRACT

The disclosure provides for peptide-based bolaamphiphile vectors that are capable of encapsulating a variety of agents, including peptides, proteins, nucleic acids, and drugs. The disclosure further provides for delivering these agents across biological membranes using the peptide-based bolaamphiphile vectors.

21 Claims, 22 Drawing Sheets

(56) References Cited

OTHER PUBLICATIONS

Figure 1F:
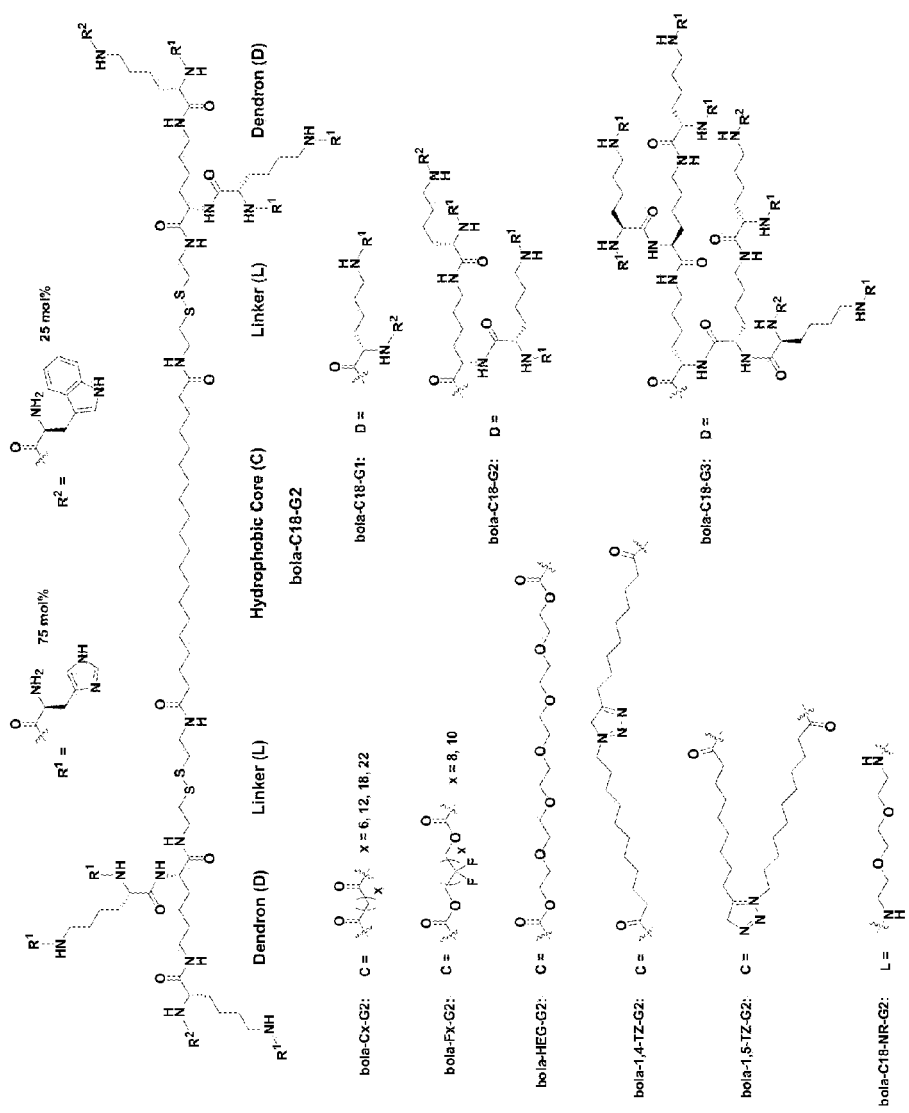

Liu et al., "Interfacial Assembly of a Series of Cinnamoyl-Containing Bolaamphiphiles: Spacer-Controlled Packing, Photochemistry, and Odd-Even Effect", Langmuir 28:3474-3482 (2012).
Love et al., "Lipid-like materials for low-dose, in vivo gene silencing", PNAS 107(5):1864-1869 (2010).
Malone et al., "Cationic liposome-mediated RNA transfection", PNAS 86:6077-6081 (1989).
Mitragotri et al., "Overcoming the challenges in administering biopharmaceuticals:formulation and delivery strategies", Nat. Rev. Drug Discovery 13:655-672 (2014).
Rejman et al., "Size-dependent internalization of particles via the pathways of clathrin and caveolae-mediated endocytosis", Biochem. J. 377:159-169 (2004).
Rozema et al., "Dynamic PolyConjugates for targeted in vivo delivery of siRNA to hepatocytes", PNAS 104 (32):12982-12987 (2007).
Sahin et al., "Combinatorial RNAi for quantitative protein network analysis", PNAS 104(16):6579-6584 (2007).
Salto et al., "Enhanced Hydrophobicity of Fluorinated Lipid Bilayer: A Molecular Dynamics Study", J. Phys. Chem B 112:11305-11309 (2008).
Silva et al., "Selective Differentiation of Neural Progenitor Cells by High-Epitope Density Nanofibers", Science 303:1352-13 (2004).
Son et al., "Bioreducible Polymers for Gene Silencing and Delivery", Accounts of Chemical Research 45 (7):1100-1112 (2012).
Tabernero et aL, "First-in-Humans Trial of an RNA Interference Therapeutic Targeting VEGF and KSP in Cancer Patients with Liver Involvement," Cancer Discovery 3:406-417 (2013).
Whitehead et al., "Knocking down barriers:advances in siRNA delivery", Nature Reviews 8:129-138 (2009).
Won et al., "Oligopeptide complex for targeted non-viral gene delivery to adipocytes", Nature Materials 13:1157-1164 (Oct. 5, 2014).
Wong et al., "Co-Injection of a Targeted, Reversibly Masked Endosomolytic Polymer Dramatically Improves the Efficacy of Cholesterol-Conjugated Small Interfering RNAs In Vivo", Nucleic Acid Therapeutics 22(6):380-390 (2012).
Wu et al., "Dendrimers as Carriers for siRNA Delivery and Gene Silencing: A Review", The Scientific World Journal (2013).
Yu et al., "An Amphiphilic Dendrimer for Effective Delivery of Small Interfering RNA and Gene Silencing In Vitro and In Vivo", Angewandte Chemie 51:8478-8484 (2012).
Zeng et al., "Multifunctional Dendronized Peptide Polymer Platform for Safe and Effective siRNA Delivery", JACS 135:4962-4955 (2013).
Ingber et al., Cell structure and hierarchical systems biology. J. Cell Sci. 116:1157-1173 (2003).
Inukai et al., Preparation and characterization of hyaluronate-hydroxyethyl acrylate blend hydrogel for controlled release device. Chem. Pharm. Bull. 48:850-854 (2000).
Ito et al., "Mesechymal Stem Cell and Islet Co-Transplantation Promotes Graft Revascularization and Function", Transplantation, 89(12):1438-1445 (Jun. 28, 2010).
Jain et al., "Lactose-ornithine bolaamphiphiles for efficient gene delivery in vitro", International Journal of Pharmaceutics 423:392-400 3 (2012).
Jun et al., Biomimetic self-assembled nanofibers Soft Matter 2:177-181 (2006).
Kersey et al., A hybrid polymer gel with controlled rates of cross-link rupture and self-repair J. R. Soc. Interface 4:373-380 (2007).
Khan et al., "Diaminododecane-based cationic bolaamphiphile as a non-viral gene delivery", Biomaterials 33, 4673-4680 (2012).
Kim et al., "Polyoxalate Nanoparticles as a Biodegradable and Biocompatible Drug Delivery Vehicle," Biomacromolecules 11:555-560 (2010).
Kim et al., "Dendronized gold nanoparticles for siRNA delivery," Small 8:3253-3256 (Nov. 2012).
Kim et al., "In Silico, In Vitro, and In Vivo Studies Indicate the Potential Use of Bolaamphiphiles for Therapeutic siRNAs Delivery," Molecular Therapy—Nucleic Acids 2:e80, (2013).
Kleinman et al., Isolation and characterization of type IV procollagen, laminin, and heparan sulfate proteoglycan from the EHS sarcoma. Biochemistry 21:6188-6193 (1982).
Kopecek, Hydrogel Biomaterials: A Smart Future? J. Biomaterials 28:5185-5192 (2007).
Kulkarni et al., "Pendant Polymer:Amino-β-Cyclodextrin:siRNA Guest:Host Nanoparticles as Efficient Vectors for Gene Silencing," J Am Chem Soc 134:7596-7599 (Apr. 30, 2012).
Lee et al., Controlling Mechanical and Swelling Properties of Alginate Hydrogels Independently by Cross-Linker Type and Cross-Linking Density Macromolecules 33,4291-4294 (2000).
Lee et al., Hydrogels for tissue engineering. J. Chem ReV 101:1869-1879 (2001).
Lee et al. Three-dimensional micropatterning of bioactive hydrogels via two-photon laser scanning photolithography for guided 3D cell migration. Biomaterials 29:2962-2968 (2008).
Lee et al., Growth factor delivery-based tissue engineering: general approaches and a review of recent developments. J R Soc Interface 8:153e70 (2011).
Liao et al., De novo design of saccharide-peptide hydrogels as synthetic scaffolds for tailored cell responses. J Am Chem Soc 131:17638e46 (2009).
Liao et al., Maintaining functional islets through encapsulation in an injectable saccharide-peptide hydrogel. Biomaterials 34(16):3984-91 (Mar. 7, 2013).
Liao et al., The effect of cell-matrix interaction on encapsulated human islets. presented at the Congress of the International Pancreas and Islet Transplantation, (Jun. 2013).
Liao et al., "The Effect of Cell-Matrix Interaction on Encapsulated Human Islets," Transplantation 96(65):S97 (Sep. 27, 2013).
Lin et al., PEG Hydrogels for the Controlled Release of Biomolecules in Regenerative Medicine Pharmacol. Res. 26:631-643 (2009).
Lin et al., Glucagon-like peptide-1 functionalized PEG hydrogels promote survival and function of encapsulated pancreatic beta-cells. Biomacromolecules 10:2460e7 (2009).
Liu et al., "SiRNA Delivery Systems Based on Neutral Cross-Linked Dendrimers," Bioconjug Chem 23:174-183 (Jan. 2012).
Liu et al., "Efficient Delivery of Sticky siRNA and Potent Gene Silencing in aProstate Cancer Model Using a Generation 5 Triethanolamine-Core PAMAM Dendrimer," Mol Pharmaceutics 9:470-481 (Mar. 2012).
Lutolf et al., Synthesis and physicochemical characterization of end-linked poly(ethylene glycol)-co-peptide hydrogels formed by Michael-type addition. Biomacromolecules 4:713-722 (2003).
Martens et al., Tailoring the degradation of hydrogels formed from multivinyl poly(ethylene glycol) and poly(vinyl alcohol) macromers for cartilage tissue engineering. Biomacromolecules 4:283-292 (2003).
Martin et al., Human embryonic stem cells express an immunogenic nonhuman sialic acid. Nat Med 11:228e32 (2005).
McCall et al., Update on islet transplantation. Cold Spring Harb Perspect Med 2:a007823 (2012).
Merkel et al., "Molecular modeling and in vivo imaging can identify successful flexible triazine dendrimer-based siRNA delivery systems," J Control Release 153(1):23-33 (2011).
Metters et al., Network formation and degradation behavior of hydrogels formed by Michael-type addition reactions Biomacromolecules 6:290-301 (2005).
Metzke et al. A novel carbohydrate-derived side-chain polyether with excellent protein resistance. J. Am. Chem. Soc. 125:7760-7761 (2003).
Metzke et al., Structure-property studies on carbohydrate-derived polymers for use as protein-resistant biomaterials. Biomacromolecules 9:208-215 (2008).
Moassesfar et al., Slide on Transplantation Medical Cost, Islets vs. Pancreas, presented before the International Pancreas & Islet Transplant Association (IPITA) Congress on Sep. 25, 2013.
Negishi et al., Luminescence technology in preservation and transplantation for rat islet. Islets 2011;3:111e7 (2011).

(56) References Cited

OTHER PUBLICATIONS

Nguyen et al., "Polymeric Materials for Gene Delivery and DNA Vaccination," Adv Mater 21:847-867 (2009).
Nguyen et al., "Nucleic acid delivery: the missing pieces of the puzzle?," Acc Chem Res 45:1153-1162 (Jul. 2012).
Nie et al., Production of heparin-containing hydrogels for modulating cell responses. Acta Biomater. 5:865-875 (2009).
Nikolova et al., The vascular basement membrane: a niche for insulin gene expression and beta cell proliferation. Dev Cell 10:397e405 (2006).
Nuttelman et al., Macromolecular monomers for the synthesis of hydrogel niches and their application in cell encapsulation and tissue engineering Prog. Polym. Sci. 33: 167-179 (2008).
Omori et al., Microassay for glucose-induced preproinsulin mRNA expression to assess islet functional potency for islet transplantation. Transplantation 89:146e54 (2010).
Paszek et al., Tensional homeostasis and the malignant phenotype. Cancer Cell 8:241-254 (2005).
Pavan et al., "Computational Insights into the Interactions between DNA and siRNA with "Rigid" and "Flexible" Triazine Dendrimers," Biomacromolecules 11: 721-730 (2010).
Pavan et al., "Dendrimers and dendrons for siRNA binding: computational insights," J Drug Deliv Sci Tec 22:83-89 (2012).
Peppas et al., Hydrogels in biology and medicine: from molecular principles to bionanotechnology AdV. Mater. 18:1345-1360 (2006).
Rackham et al., Co-transplantation of mesenchymal stem cells maintains islet organisation and morphology in mice. Diabetologia 54:1127-1135 (2011).
Rajeswari et al., "Does Tryptophan Intercalate in DNA? A Comparative Study of Peptide Binding to Alternating and Nonalternating A*T Sequences," Biochemistry 26:6825-6831 (1987).
Reed et al., In situ mechanical interferometry of matrigel films. Langmuir 25:36-39 (2009).
Rehfeldt et al., Cell responses to the mechanochemical microenvironment—implications for regenerative medicine and drug delivery. AdV. Drug DeliVery ReV. 59:1329-1339 (2007).
Rettig et al., "Progress Toward In Vivo Use of siRNAs-II," Mol Ther 20:483-512 (Mar. 2012).
Akinc et al., "A combinatorial library of lipid-like materials for delivery of RNAi therapeutics," Nat Biotechnol 26:561-569 (2008).
Ashcroft et al., Glucose metabolism in mouse pancreatic islets. Biochem J 118:143e54 (1970).
Banerjee et al. The influence of hydrogel modulus on the proliferation and differentiation of encapsulated neural stem cells. Biomaterials 30:4695-4699 (2009).
Banwell et al., Rational design and application of responsive alpha-helical peptide hydrogels. Nat. Mater. 8:596-600 (2009).
Barnard et al., Degradable Self-Assembling Dendrons for Gene Delivery: Experimental and Theoretical Insights into the Barriers to Cellular Uptake J Am Chem Soc 133:20288-20300 (2011).
Behr, J. P., "Synthetic Gene Transfer Vectors II: Back to the Future," Acc Chem Res 45:980-984 (Feb. 2012).
Bennet et al., Incompatibility between human blood and isolated islets of Langerhans: a finding with implications for clinical intraportal islet transplantation? Diabetes 48:1907e14 (1999).
Blomeier et al. Polymer scaffolds as synthetic microenvironments for extrahepatic islet transplantation. Transplantation 82:452e9 (2006).
Borg et al., The use of biomaterials in islet transplantation. Curr Diab Rep 11:434e44 (2011).
Brown et al. Importance of hepatic portal circulation for insulin action in streptozotocin-diabetic rats transplanted with fetal pancreases. J Clin Invest 64:1688e94 (1979).
Brunelle et al., "A structureeactivity investigation of hemifluorinated bifunctional bolaamphiphiles designed for gene delivery," C. R. Chimie 12:88-208 (2009).
Bryant et al., Hydrogel properties influence ECM production by chondrocytes photoencapsulated in poly(ethylene glycol) hydrogels. J. Biomed. Mater Res. 59:63-72 (2002).

Bryant et al., Incorporation of tissue-specific molecules alters chondrocyte metabolism and gene expression in photocrosslinked hydrogels. Ada Biomater. 1:243-252 (2005).
Burdick et al. Photoencapsulation of osteoblasts in injectable RGD-modified PEG hydrogels for bone tissue engineering Biomaterials 23:4315-4323 (2002).
Burdick et al. Controlled degradation and mechanical behavior of photopolymerized hyaluronic acid networks. Biomacromolecules 6:386-391 (2005).
Burnett et al., "RNA-based Therapeutics—Current Progress and Future Prospects," J. Chem Biol 19:60-71 (Jan. 2012).
Carlsson et al., Markedly decreased oxygen tension in transplanted rat pancreatic islets irrespective of the implantation site. Diabetes 50:489e95 (2001).
Chang et al., "Surface-Engineered Dendrimers with a Diaminododecane Core Achieve Efficient Gene Transfection and Low Cytotoxicity," Bioconjugate Chemistry 25(2):342-50. Jan. 21, 2014).
Chawla et al., Biodegradable and biocompatible synthetic saccharide-Peptide hydrogels for three-dimensional stem cell culture. Biomacromolecules 12:560e7 (2011).
Chawla et al., Modulation of chondrocyte behavior through tailoring functional synthetic saccharide-peptide hydrogels. Biomaterials 33:6052e60 (Sep. 1, 2012).
Chen et al., "Bioreducible Hyperbranched Poly(amido amine)s for Gene Delivery," Biomacromolecules 10:2921-2927 (2009).
Cordero Garcia, Marcela M. Non-final Office Action for U.S. Appl. No. 14/186,973 (dated Mar. 24, 2015).
Cordero Garcia, Marcela M. Final Office Action for U.S. Appl. No. 14/186,973 (dated Aug. 21, 2015).
Cordero Garcia, Marcela M. Notice of Allowance for U.S. Appl. No. 14/186,973 (dated Nov. 12, 2016).
Creusat et al., "Self-Assembling Polyethylenimine Derivatives Mediate Efficient siRNA Delivery in Mammalian Cells," Chembiochem 9:2787-2789 (2008).
Crombez et al., "Targeting cyclin B1 through peptide-based delivery of siRNA prevents tumour growth," Nucleic Acids Res 37(14):4559-4569 (2009).
Cui et al., "Conjugation Chemistry through Acetals toward a Dextran-Based Delivery System for Controlled Release of siRNA," J Am Chem Soc 134:15840 (Sep. 2012).
Davis et al., "Evidence of RNAi in humans from systemically administered siRNA via targeted nanoparticles," Nature 464:1067-1071 (2010).
Deforest et al., S. Sequential click reactions for synthesizing and patterning three-dimensional cell microenvironments. Nat. Mater. 8:659-664 (2009).
Degoricija et al., Hydrogels for osteochondral repair based on photocrosslinkable carbamate dendrimers. Biomacromolecules 9:2863-2872 (2008).
Denyelle et al., "Synthesis and preliminary biological studies of hemifluorinated bifunctional bolaamphiphiles designed for gene delivery," New Journal of Chemistry 30:629-646 (2006).
Discher et al., Tissue cells feel and respond to the stiffness of their substrate. Science 310:1139-1143 (2005).
Drury et al., Hydrogels for tissue engineering: scaffold design variables and applications. J. Biomaterials 24:4337-4351 (2003).
Dunn et al., "Reductively-responsive siRNA-conjugated hydrogel nanoparticles for gene silencing," J Am Chem Soc 134:7423-7430 (May 2012).
Economic costs of diabetes in the U.S. in 2007. Diabetes Care 31:596e 615 (2008).
Elbert et al., Conjugate addition reactions combined with free-radical cross-linking for the design of materials for tissue engineering. Biomacromolecules 2:430-441 (2001).
Engler et al., Matrix elasticity directs stem cell lineage specification. Cell 126:677-689 (2006).
Fabio et al., "Novel Galactosylated Polyamine Bolaamphiphiles for Gene Delivery," Bioconjugate Chemistry 14:358-367 (2003).
Fischer et al., "Dendritic Polyglycerols with Oligoamine Shells Show Low Toxicity and High siRNA Transfection Efficiency in Vitro," Bioconjug Chem 21:1744-1752 (2010).

(56) References Cited

OTHER PUBLICATIONS

Flanagan et al., Neurite branching on deformable substrates. NeuroReport 13: 2411-2415 (2002).
Frisch et al., Anoikis mechanisms. Curr Opin Cell Biol 13:555e62 (2001).
Gaucheron et al., "In Vitro Gene Transfer with a Novel Galactosylated Spermine Bolaamphiphile," Bioconjugate Chem. 12:569-575 (2001).
Gelain et al., Designer self-assembling peptide nanofiber scaffolds for adult mouse neural stem cell 3-dimensional cultures. S. PLoS One 1:e119 (2006).
Griesfiaber et al., Synthesis and Characterization of Elastin-Mimetic Hybrid Polymers with Multiblock, Alternating Molecular Architecture and Elastomeric Properties. Macromolecules 42:2532-2541(2009).
Guilak et al., Control of stem cell fate by physical interactions with the extracellular matrix. Cell Stem Cell 5,17-26 (2009).
Haines-Butterick et al., Controlling hydrogelation kinetics by peptide design for three-dimensional encapsulation and injectable delivery of cells. Proc. Natl. Acad. Sci. U.S.A. 104:7791-7796 (2007).
Hiemstra et al., Rapidly in situ forming biodegradable robust hydrogels by combining stereocomplexation and photopolymerization. J. Am. Chem. Soc. 129:9918-9926 (2007).
Hu et al., Rational design of transglutaminase substrate peptides for rapid enzymatic formation of hydrogels. J. Am. Chem. Soc. 125,14298-14299 (2003).
Hu et al., Hydrogels cross-linked by native chemical ligation. Biomacromolecules 2194-2200 (2009).
Hwang et al., Cartilage tissue engineering: Directed differentiation of embryonic stem cells in three-dimensional hydrogel culture. J. Methods Mol. Biol. 407:351-373 (2007).
Rizzi et al., Recombinant protein-co-PEG networks as cell-adhesive and proteolytically degradable hydrogel matrixes. Part I: Development and physicochemical characteristics. Biomacromolecules 6:1226-1238 (2005).
Salvay et al., Extracellular matrix protein-coated scaffolds promote the reversal of diabetes after extrahepatic islet transplantation. Transplantation 85:1456e64 (2008).
Schafer et al., "Redox environment of the cell as viewed through the redox state of the glutathione disulfide/glutathione couple," Free Rad. Biol. Med. 30:1191-1212 (2001).
Schaffer et al., "Molecular Engineering of Viral Gene Delivery Vehicles,"Annu Rev Biomed Eng 10:169-194 (2008).
Schense et al., Cross-linking exogenous bifunctional peptides into fibrin gels with factor XIIIa. Bioconjugate Chem. 10:75-81 (1999).
Schnizer, Richard A. Non-Final Office Action for U.S. Appl. No. 14/221,249 (dated Nov. 25, 2015).
Schnizer, Richard A. Final Office Action for U.S. Appl. No. 14/221,249 (dated May 2, 2016).
Schnizer, Richard A. Advisory Action for U.S. Appl. No. 14/221,249 (dated Jul. 22, 2016).
Schnizer, Richard A. Non-Final Office Action for U.S. Appl. No. 14/221,249 (dated Sep. 20, 2016).
Seliktar D. Designing cell-compatible hydrogels for biomedical applications. Science 336:1124e8 (Jun. 15, 2012).
Silva et al., Selective differentiation of neural progenitor cells by high-epitope density nanofibers. Science 303:1352-1355 (2004).
Smith et al., "Diblock Glycopolymers Promote Colloidal Stability of Polyplexes and Effective pDNA and siRNA Delivery under Physiological Salt and Serum Conditions," Biomacromolecules 12:3015-3022 (2011).
Solon et al. Fibroblast adaptation and stiffness matching to soft elastic substrates. Biophys. J. 93:4453-4461 (2007).
Son et al., "Bioreducible Polymers for Gene Silencing and Delivery," J. Acc Chem Res 45:1100-1112 (2011).
Sonawane et al., "Chloride Accumulation and Swelling in Endosomes Enhances DNA Transfer by Polyamine-DNA Polyplexes," J Biol Chem 278:44826-44831 (2003).
Soofi et al., The elastic modulus of Matrigel as determined by atomic force microscopy. J. Stud. Biol. 167:216-219 (2009).
Stendahl et al., Extracellular matrix in pancreatic islets: relevance to scaffold design and transplantation. Cell Transplant 18:1e12 (2009).
Su et al., Anti-inflammatory peptide-functionalized hydrogels for insulin-secreting cell encapsulation. Biomaterials 31:308e14 (2010).
Tan et al., Thermosensitive injectable hyaluronic acid hydrogel for adipose tissue engineering. Biomaterials 30 (36):6844-6853 (2009).
Tang et al., "In Vitro Gene Delivery by Degraded Polyamidoamine Dendrimers," Bioconjugate Chem 7:703-714 (1996).
Tibbet et al., Hydrogels as Extracellular Matrix Mimics for 3D Cell Culture. Biotechnol Bioeng. 103(4):655-663 (2009).
Toyofuku et al., Natural killer T-cells participate in rejection of islet allografts in the liver of mice. Diabetes 55:34e9 (2006).
Urakami et al.,Living Ring-Opening Polymerization of a Carbohydrate-Derived Lactone for the Synthesis of Protein-Resistant Biomaterials. Biomacromolecules, Jan. 26, 2008, 9, 592-597.
Vercruysse et al. Synthesis and in vitro degradation of new polyvalent hydrazide cross-linked hydrogels of hyaluronic acid. Bioconjugate Chem. 8:686-694 (1997).
Wagner, E., "Polymers for siRNA Delivery: Inspired by Viruses to be Targeted, Dynamic, and Precise," Acc Chem Res 45:1005-1013 (2011).
Wakefield et al., "Membrane Activity and Transfection Ability of Amphipathic Polycations as a Function of Alkyl Group Size," Bioconjug Chem 16:1204-1208 (2005).
Wang et al. Substrate flexibility regulates growth and apoptosis of normal but not transformed cells. Am. J. Physiol. Cell Physiol. 279:C1345-1350 (2000).
Weber et al., Cell-matrix interactions improve Beta-cell survival and insulin secretion in three-dimensional culture. Tissue Eng Part A 14:1959e68 (2008).
Yamaguchi et al., Growth Factor Mediated Assembly of Cell Receptor-Responsive Hydrogels J. Am. Chem. Soc. 129:3040-3041 (2007).
Zeng et al. "Multifunctional Dendronized Peptide Polymer Platform for Safe and Effective siRNA Delivery", JACS 135:4962-4965 (Mar. 15, 2013).

\* cited by examiner

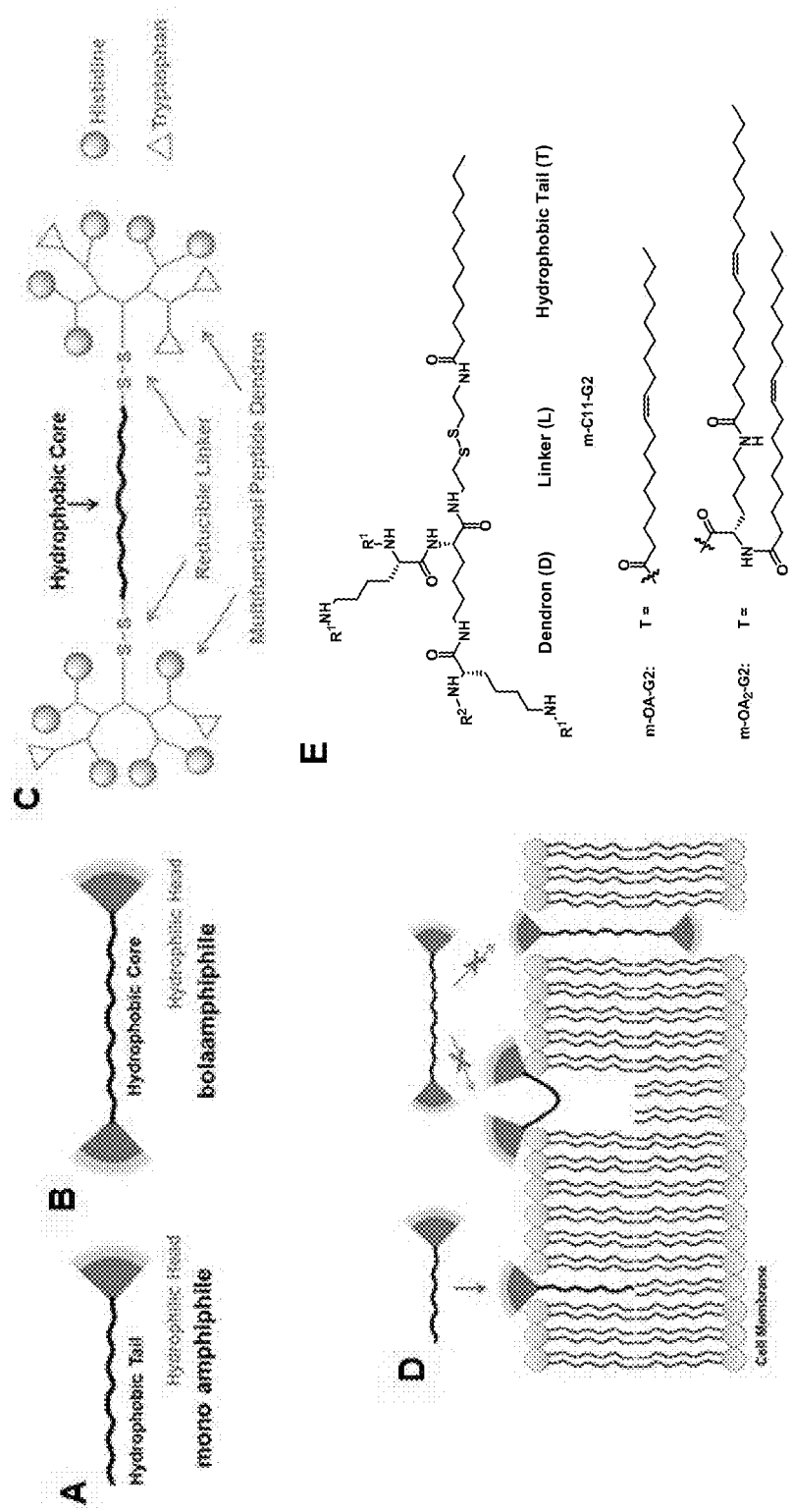
FIGURE 1A-E

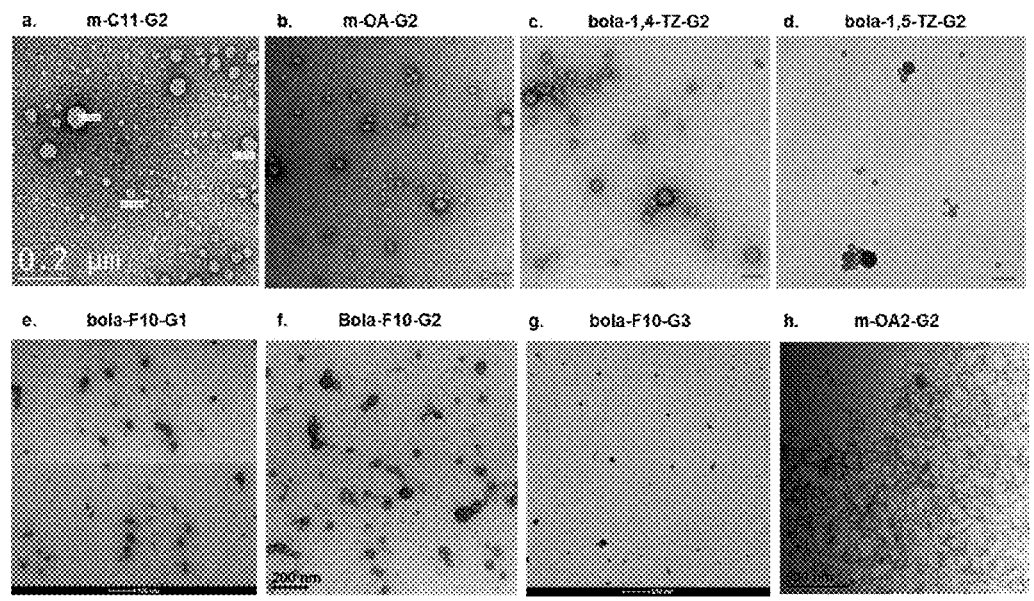
FIGURE 11A-H
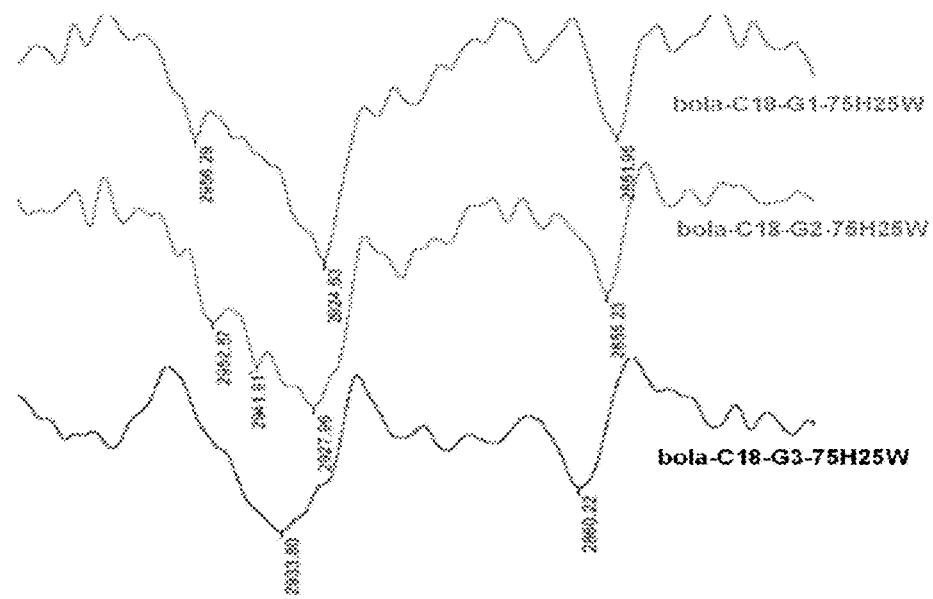
FIGURE 12

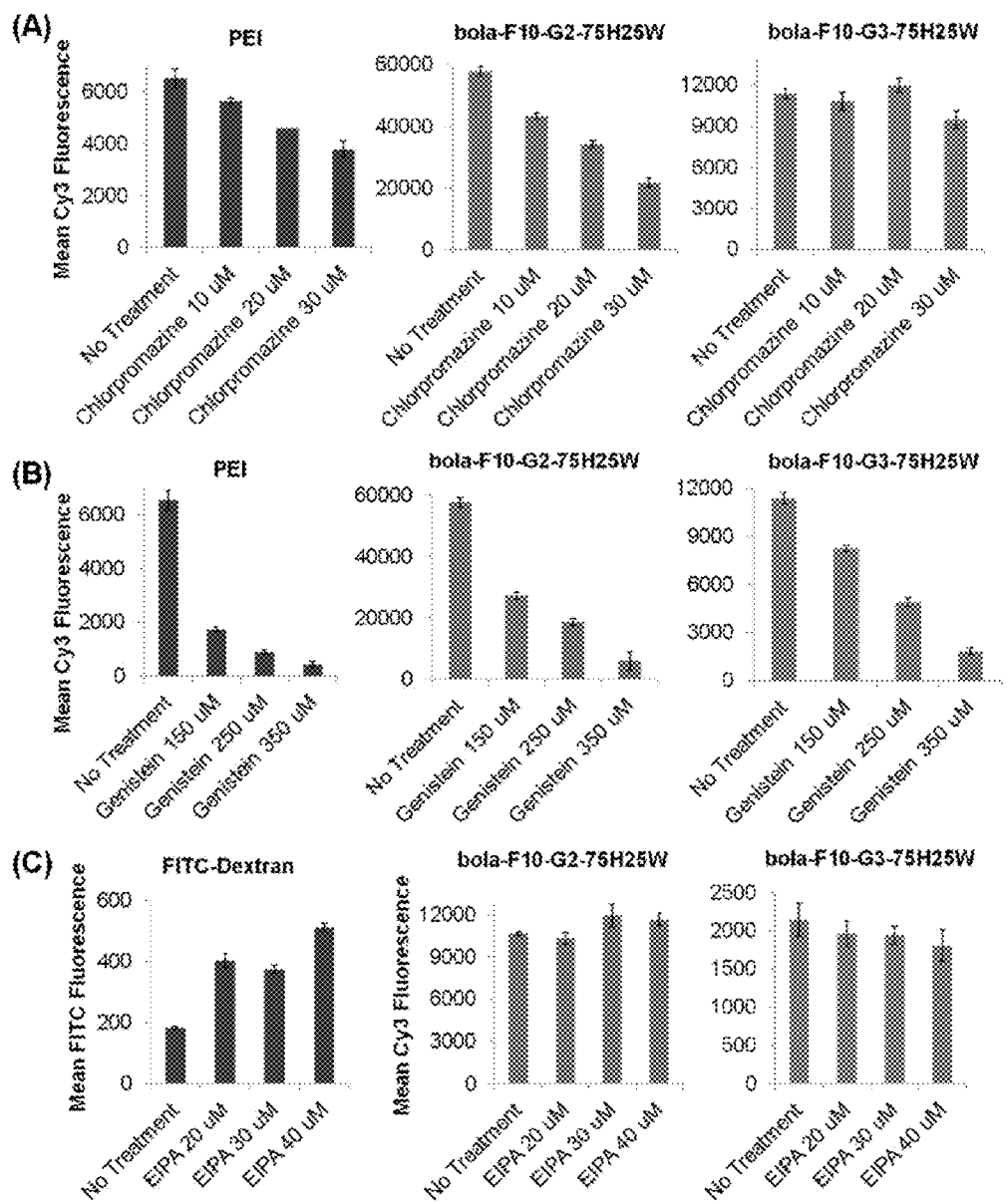
FIGURE 15A-C

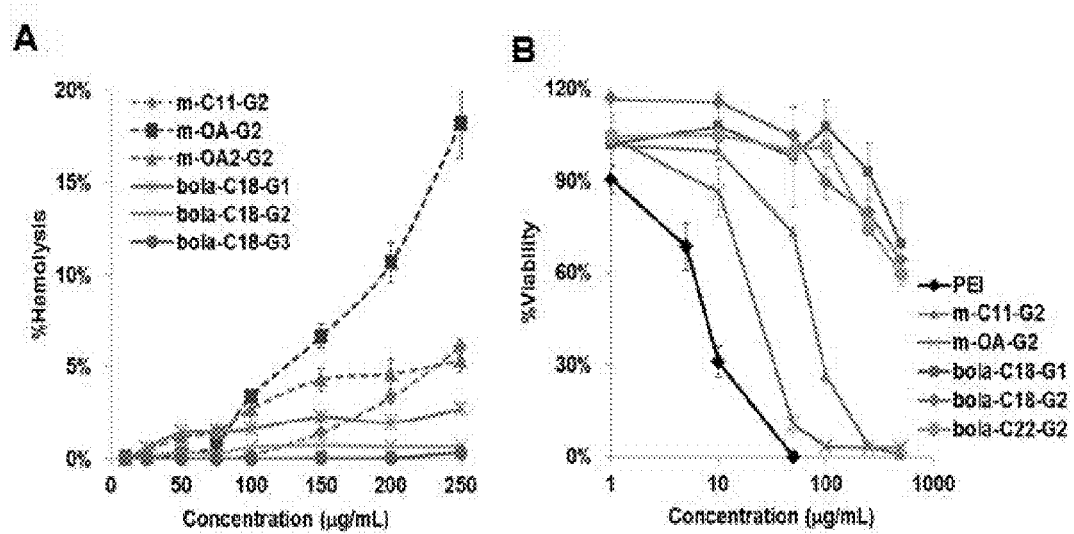
FIGURE 16A-B

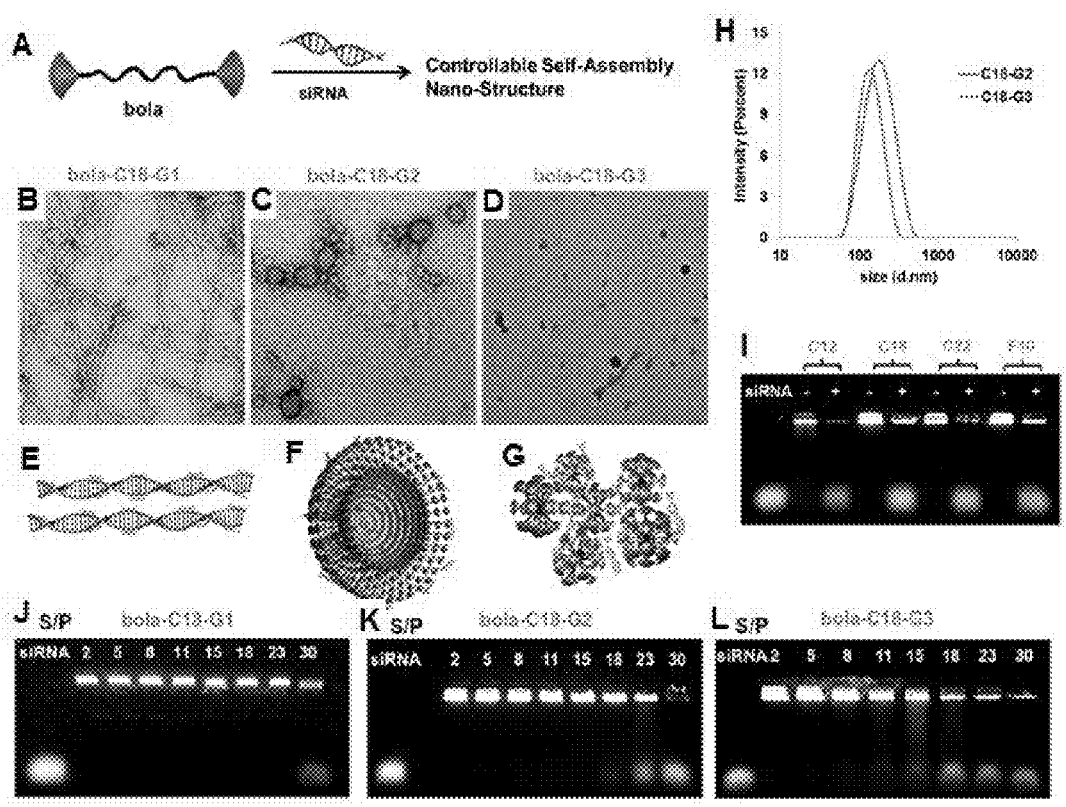
FIGURE 17A-L

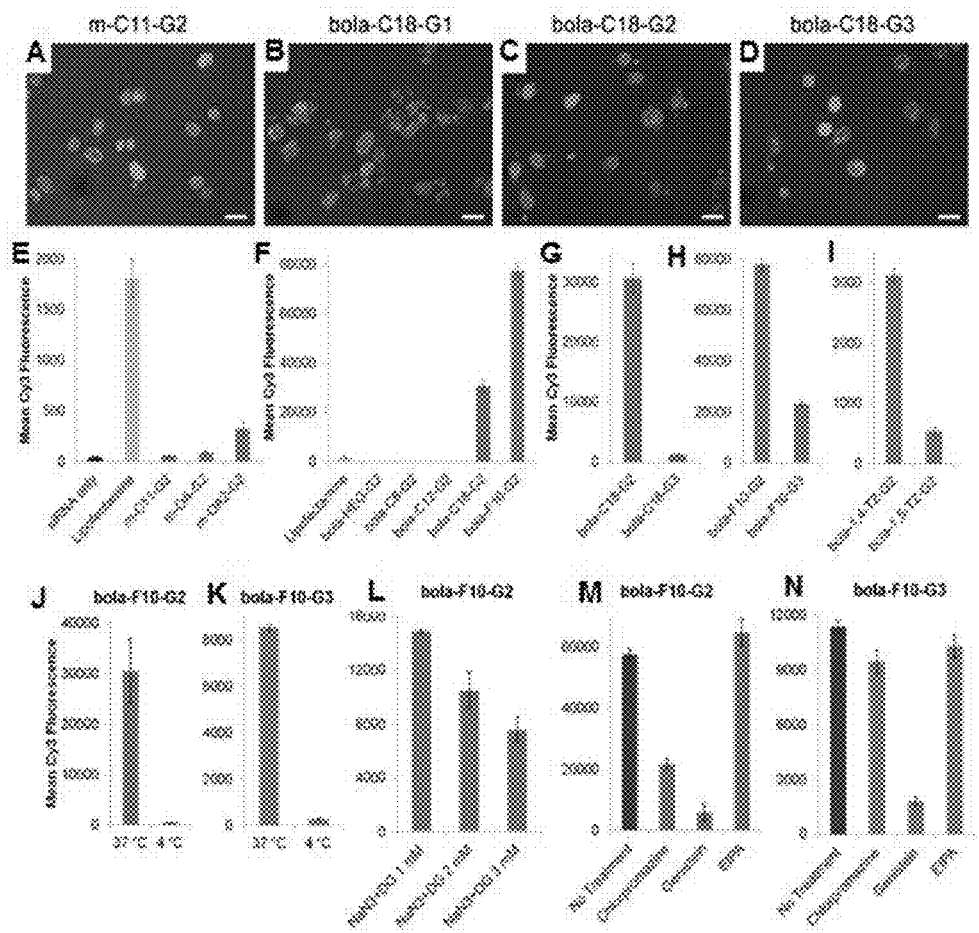
FIGURE 18A-N

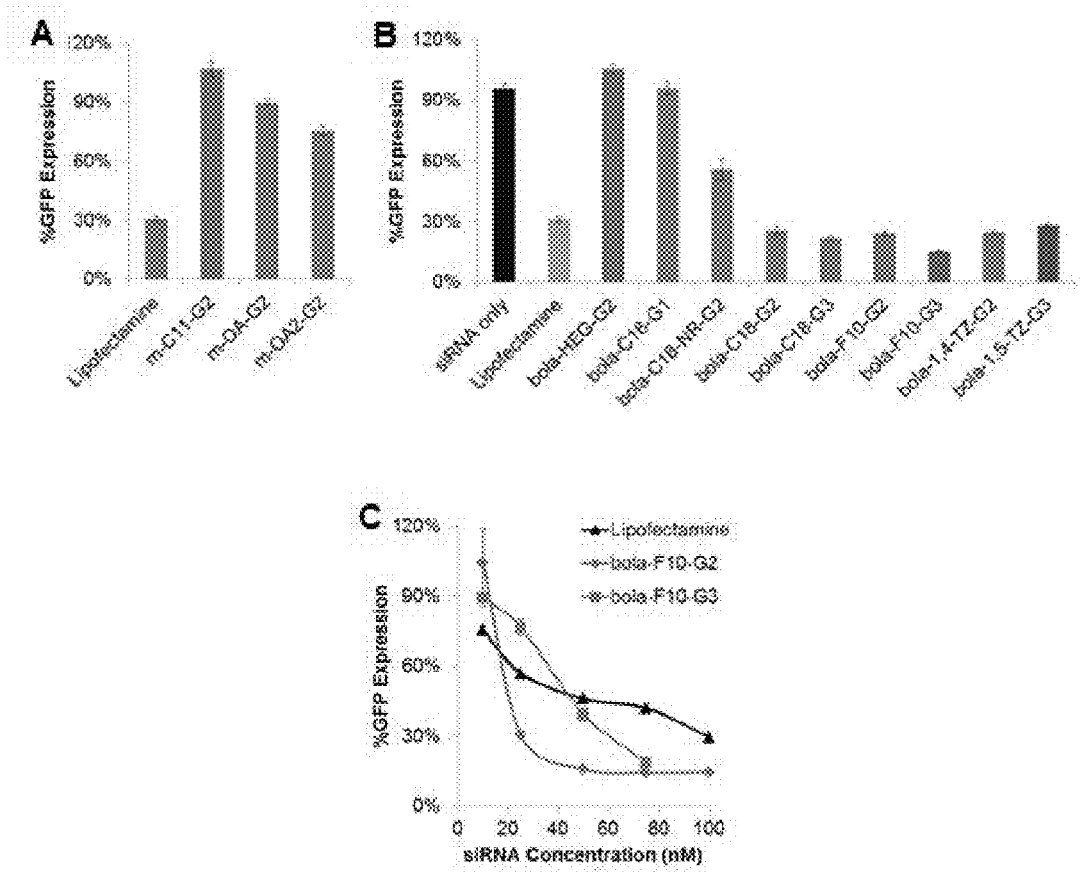
FIGURE 19A-C

C
Natural Amino Acids/Compounds
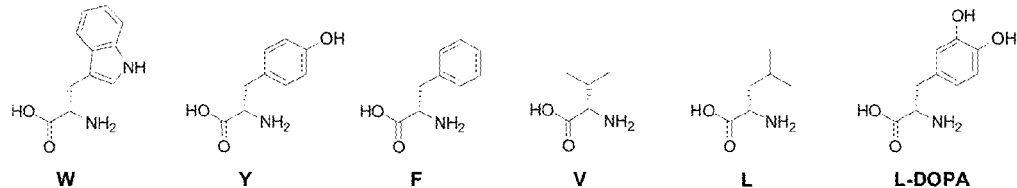
Trp/Tyr Derivatives
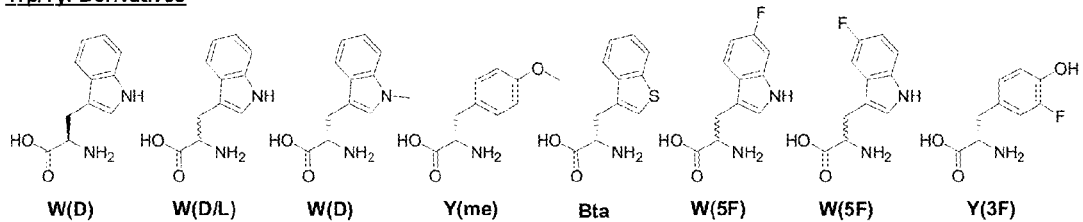
4-Phe Derivatives
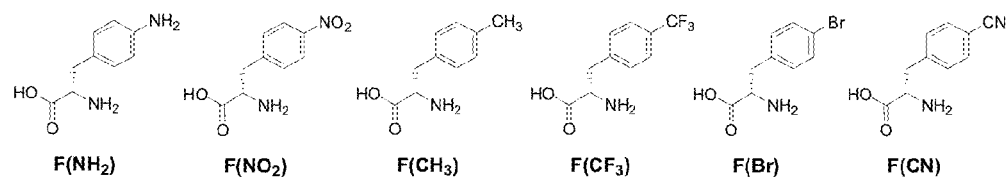
Other Aromatic Amino Acids
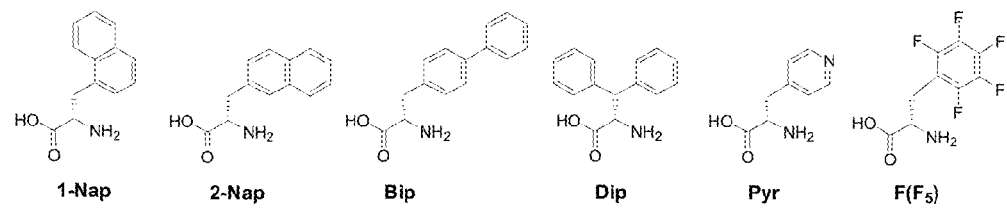
FIGURE 20C

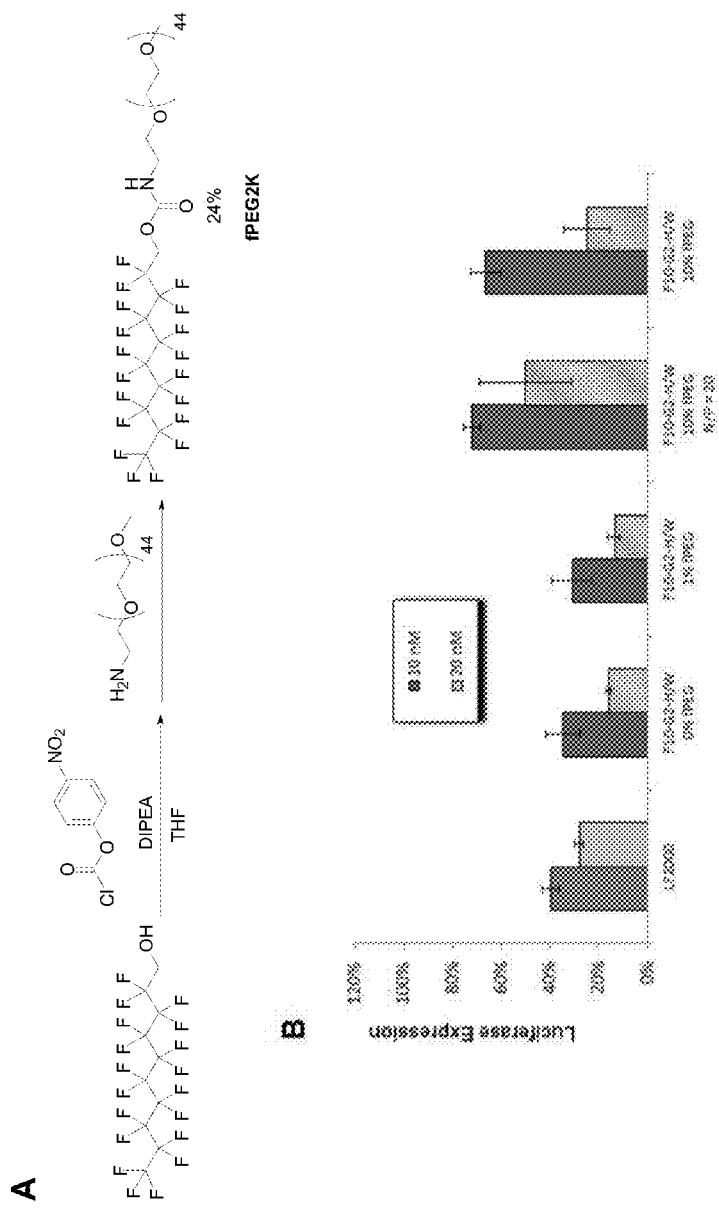
FIGURE 21A-B

| F10-G2-H/W | 0 m d (nm) | 0 m PDI | 30 m d (nm) | 30 m PDI | 90 m d (nm) | 90 m PDI | 360 m d (nm) | 360 m PDI |
|---|---|---|---|---|---|---|---|---|
| 0% | 145.9 | 0.199 | 176.8 | 0.215 | 341.3 | 0.249 | 709.3 | 0.272 |
| 1% fPEG2K | 128.2 | 0.143 | 154.3 | 0.167 | 207.7 | 0.124 | 300.5 | 0.213 |
| 10% fPEG2K | 159.4 | 0.238 | 161.2 | 0.198 | 156.1 | 0.138 | 189.7 | 0.119 |

FIGURE 21C

VECTORS FOR DELIVERY OF AGENTS ACROSS BIOLOGICAL MEMBRANES

CROSS REFERENCE TO RELATED APPLICATIONS

This application claims priority under 35 U.S.C. §119 from Provisional Application Ser. No. 62/031,158, filed Jul. 30, 2014, the disclosure of which is incorporated herein by reference.

STATEMENT AS TO FEDERALLY SPONSORED RESEARCH

This invention was made with Government support under Grant No. DK098446, awarded by the National Institutes of Health. The Government has certain rights in this invention

TECHNICAL FIELD

The disclosure provides for peptide-based bolaamphiphile vectors that are capable of encapsulating a variety of agents, including peptides, proteins, nucleic acids, and drugs. The disclosure further provides for delivering these agents across biological membranes using the peptide-based bolaamphiphile vectors.

BACKGROUND

RNAi has tremendous potential for therapeutic treatment options. The lack of safe and efficient intracellular delivery vectors, however, has significantly hampered the potential of siRNA technology. For example, current viral-based vectors have serious concerns of immunogenicity and infection, while current synthetic vectors are often cytoxic and generally exhibit low efficiency in gene knockdown.

SUMMARY

Disclosed herein is an innovative family of peptide-based bolaamphiphiles (bola) as carriers for safe and effective delivery of small and large molecules across biological membranes. In some embodiments, the compounds of the disclosure provide for effective delivery of nucleic acids, such as siRNA, into cells. In other embodiments, the compounds of the disclosure provide for the delivery across biological membranes of nucleotide or nucleoside therapeutics (e.g., deoxyadenosine analogues; adenosine analogs, deoxycytidine analogues, guanosine and deoxyguanosine analogs, thymidine and deoxythymidine analogues, dexoyuridine analogs, nucleobase analogs, and nucleotide analogues); peptide or protein based therapeutic agents (e.g., insulin, insulin analogs, cytokines, growth factors, and analgesics); and small molecule therapeutics.

Conventional amphiphiles used for gene delivery are generally composed of hydrophilic headgroup(s) on one side of the molecule and hydrophobic tail(s) on the other. Bolaamphiphiles, instead, are composed of two hydrophilic headgroups on each end of the molecule connected by a hydrophobic core. The molecular structures of the compounds disclosed herein are non-membrane disruptive and greatly reduce the toxicity associated with traditional amphiphilic vectors. Furthermore, there was a direct structure-property relationship between the molecular structure of the compounds of the disclosure and their self-assembly behavior and subsequent biological activity. The compounds disclosed herein were found to be effective in vitro in silencing gene expression at low siRNA concentrations.

In a particular embodiment, the disclosure provides for a compound comprising the formula: $D^1\text{-}(L^1)_x\text{-}C\text{-}(L^2)_y\text{-}D^2$: wherein, $D^1$ and $D^2$ are dendritic hydrophilic head groups comprising a plurality of linked peptides, wherein the head groups comprise two or more different peptides and wherein the head groups comprise one to six generations of branching; 'C' is a hydrophobic core comprising an optionally substituted ($C_6$ to $C_{25}$)alkyl, optionally substituted ($C_6$ to $C_{25}$)heteroalkyl, optionally substituted ($C_6$ to $C_{25}$)alkenyl, optionally substituted ($C_6$ to $C_{25}$)heteroalkenyl, optionally substituted ($C_6$ to $C_{25}$)alkynyl, optionally substituted ($C_6$ to $C_{25}$)heteroalkynyl, optionally substituted cycloalkyl, optionally substituted aryl, and optionally substituted heterocycle; and $L^1$ and $L^2$ are linkers comprising a biodegradable group that is capable of being cleaved in the cytoplasm of a cell; x is selected from 0 to 5; and y is selected from 0 to 5. In other embodiments, the head groups comprise 1, 2, 3, 4, 5, 6, 7, 8, 9, or 10 generations of branching—or a range between any two numbers of the foregoing. In a further embodiment, the compound disclosed herein comprise a hydrophobic core 'C' that is selected from:

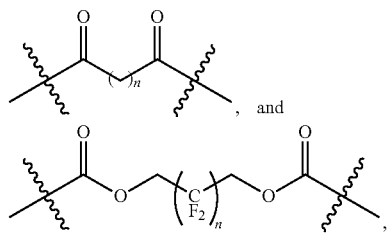

wherein, n is an integer from 6 to 25. In yet a further embodiment, the compound disclosed herein comprise a hydrophobic core 'C' having the structure:

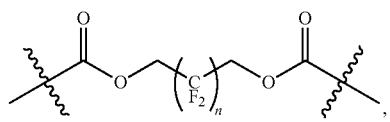

wherein n is an integer from 6 to 20. In other embodiments, n is an integer selected from 6, 7, 8, 9, 10, 11, 12, 13, 14, 15, 16, 17, 18, 19, 20, 21, 22, 23, 24, 25 or 26—or a range between any two numbers of the foregoing. In other embodiments, the length of hydrophobic core 'C' is significantly shorter than the width of a typical cell membrane.

In a particular embodiment, the disclosure also provides for a compound having the formula $D^1\text{-}(L^1)_x\text{-}C\text{-}(L^2)_y\text{-}D^2$: where x or y is an integer of >1, and $L^1$ and $L^2$ comprises a biodegradable bond selected from the group, including but not limited to, disulfide, ester, thioester, carbamate, thiocarbamate, and amide. In a further embodiment, $L^1$ and $L^2$ comprises the structure of:

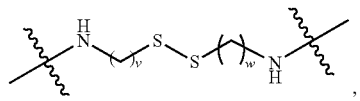

wherein v and w are independently an integer independently selected from 1, 2, 3, 4, 5, 6, 7, 8, 9, or 10. In a certain embodiment, the disclosure further provides for a compound having the formula $D^1\text{-}(L^1)_x\text{-}C\text{-}(L^2)_y\text{-}D^2$: wherein $D^1$ and/or $D^2$ comprise a plurality of linked D/L-arginine, D/L-histidine, D/L-lysine, D/L-aspartic acid, D/L-glutamic acid, D/L-serine, D/L-threonine, D/L-asparagine, D/L-glutamine, D/L-cysteine, D/L-selenocysteine, D/L-alanine, D/L-isoleucine, D/L-leucine, D/L-methionine, D/L-valine residues, and/or any analog thereof. Examples of analogs of the foregoing, include substitutions on the side chains of the amino acids, such as —NH$_2$, —OH, —COOH, —SH, —SeH, and —COH. In a further embodiment, $D^1$ and $D^2$ comprise a plurality of linked D/L-lysine residues. In yet a further embodiment, $D^1$ and/or $D^2$ also comprise histidine residues and/or aromatic amino acid residues. In particular embodiment, $D^1$ and $D^2$ comprise from 5 mol % to 95 mol % of histidine residues to 95 mol % to 5 mol % percent of aromatic amino acid residues. In other embodiments, $D^1$ and $D^2$ comprise from 10 mol % to 90 mol % of histidine residues to 90 mol % to 10 mol % percent of aromatic amino acid residues; from 15 mol % to 85 mol % of histidine residues to 85 mol % to 15 mol % percent of aromatic amino acid residues; from 20 mol % to 80 mol % of histidine residues to 80 mol % to 20 mol % percent of aromatic amino acid residues; from 25 mol % to 75 mol % of histidine residues to 75 mol % to 25 mol % percent of aromatic amino acid residues; from 30 mol % to 70 mol % of histidine residues to 70 mol % to 30 mol % percent of aromatic amino acid residues; from 35 mol % to 65 mol % of histidine residues to 65 mol % to 35 mol % percent of aromatic amino acid residues; from 40 mol % to 60 mol % of histidine residues to 60 mol % to 40 mol % percent of aromatic amino acid residues; from 45 mol % to 55 mol % of histidine residues to 55 mol % to 45 mol % percent of aromatic amino acid residues; and from 50 mol % histidine residues to 50 mol % of aromatic amino acid residues. In a certain embodiment, a compound disclosed herein comprises aromatic amino acid residues selected from:

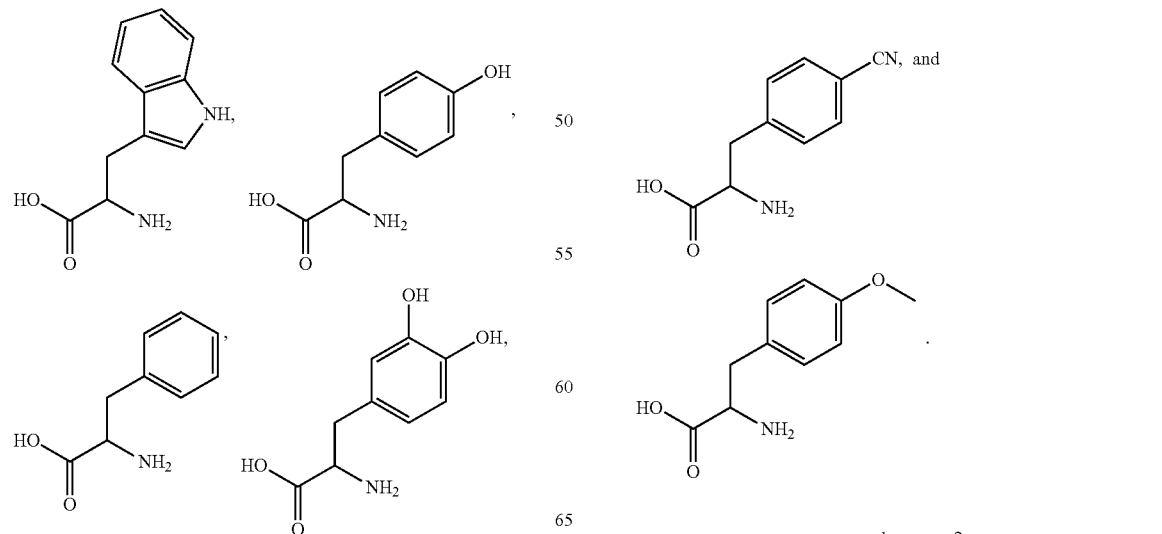

In a particular embodiment, $D^1$ and $D^2$ comprises the structure of Formula I or Formula II:

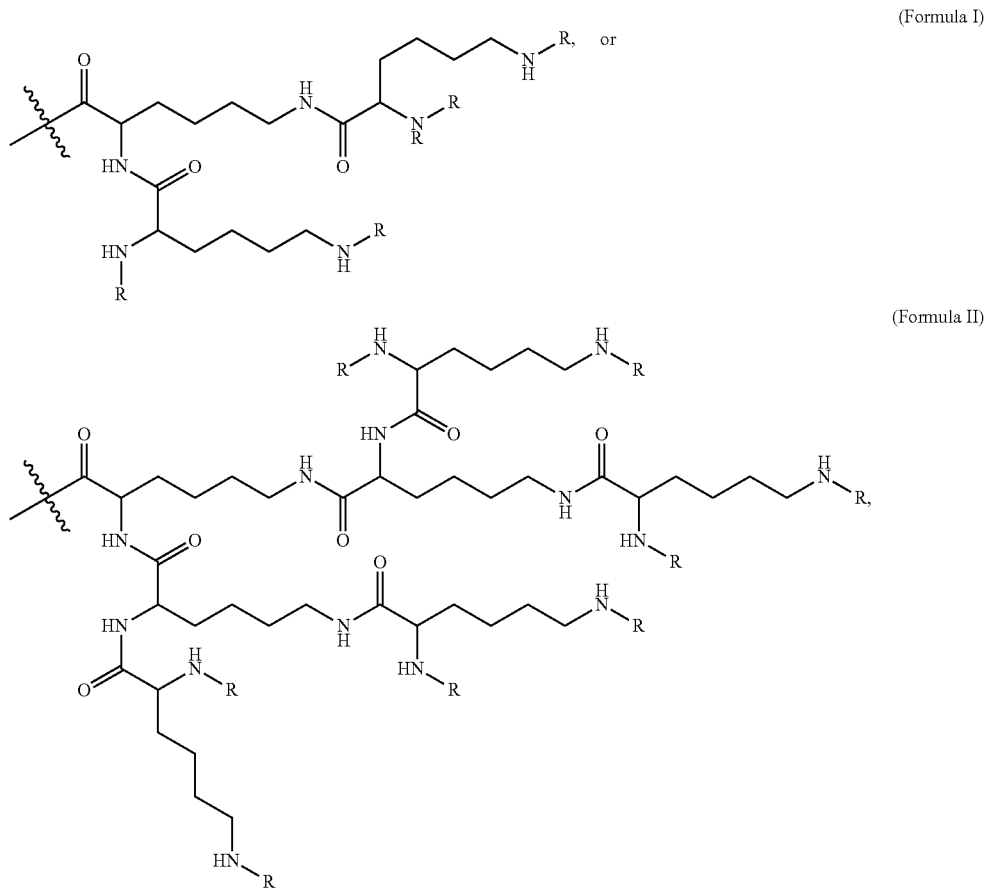

(Formula I)

(Formula II)

wherein at least one of the R groups is a histidine residue and at least one of R groups is an aromatic amino acid residue. In a further, embodiment, for Formula I or Formula II, from 10 mol % to 90 mol % of the R groups are histidine residues while 90 mol % to 10 mol % percent of the R groups are aromatic amino acid residues.

In a particular embodiment, the disclosure provides for a compound disclosed herein that further comprises an encapsulated peptide, protein, nucleic acid, or drug. In a further embodiment, a compound disclosed herein further comprises encapsulated nucleic acids. In yet a further embodiment, a compound disclosed herein further comprises encapsulated siRNA.

Figure 3:
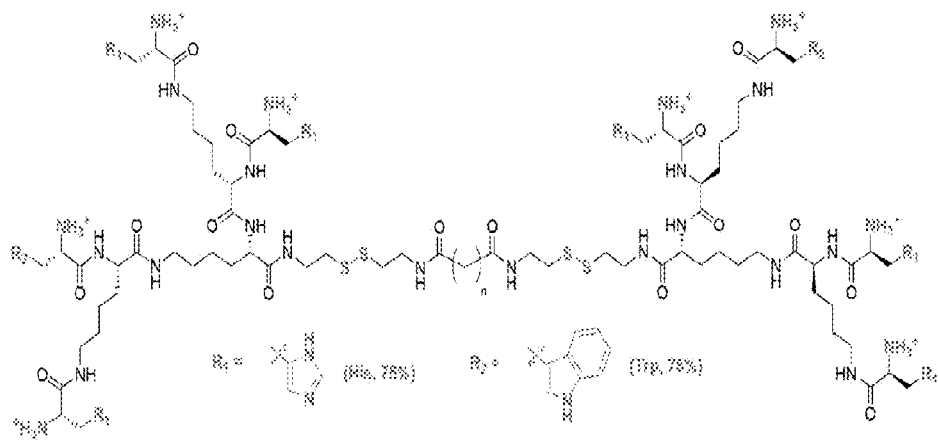

In a certain embodiment, the disclosure also provides methods for delivering a peptide, protein, nucleic acid, or drug across a biological membrane, comprising: contacting the biological membrane with a compound disclosed herein that further comprises an encapsulated peptide, protein, nucleic acid, or drug. In another embodiment, the disclosure provides a method for delivering siRNA into a cell, comprising contacting the cell (in vitro or in vivo) with a compound disclosed herein that further comprises encapsulated siRNA. Examples of siRNAs that can be used with the compounds disclosed herein, include but are not limited to siRNAs that target expression of KSP, VEGF, EphA2, PKN3, PLK1, VP24, VP35, Zaire Ebola L-polymerase, RSV nucleocapsid, ApoB, PCSK9, TTR, RRM2, K6a, VEGFR1, CASP2, p53, KRAS, TRPV1, ADRB2, CTNNB1, CTGF, TTR, and conserved regions of HBV.

In a particular embodiment, the disclosure further provides for a pharmaceutical composition comprising a compound disclosed herein which further comprises an encapsulated peptide, protein, nucleic acid, or drug and a pharmaceutically acceptable carrier.

In a certain embodiment, the disclosure provides a method of treating a disease or disorder in a subject comprising administering the pharmaceutical composition disclosed herein. Examples of such diseases or disorders include but are not limited to, diabetes; cancer; infectious and parasitic diseases; inflammatory diseases; neurodegenerative diseases; autoimmune diseases; respiratory diseases; endocrine diseases; eye diseases; intestinal diseases; cardiovascular diseases; idiopathic diseases; genetic disorders; growth disorders; congenital disorders; mental or behavioral disorders; adrenal disorders; thyroid disorders; calcium homeostasis disorders; pituitary gland disorders; and sex hormone disorders.

DESCRIPTION OF DRAWINGS

FIG. 1A-F provides an overview of the design and structure of peptide-based bolaamphiphiles. (A) and (B) schematic illustration of a mono amphiphile and a bolaamphiphile. (C) Design of peptide bolaamphiphiles. (D) Proposed different membrane insertion behavior of mono and bola amphiphiles. (E) Structure of control mono amphiphiles. (F) Structure of different peptide bolas.

FIG. 2 presents a general synthetic route to produce peptide bolaamphiphiles of the disclosure.

FIG. 3 provides an embodiment of a His-Trp functionalized bola of the disclosure, where n=6, C6-G2-75H25W; n=12, C12-G2-75H25W; n=18, C18-G2-75H25W; n=22, C22-G2-75H25W.

Figure 4:
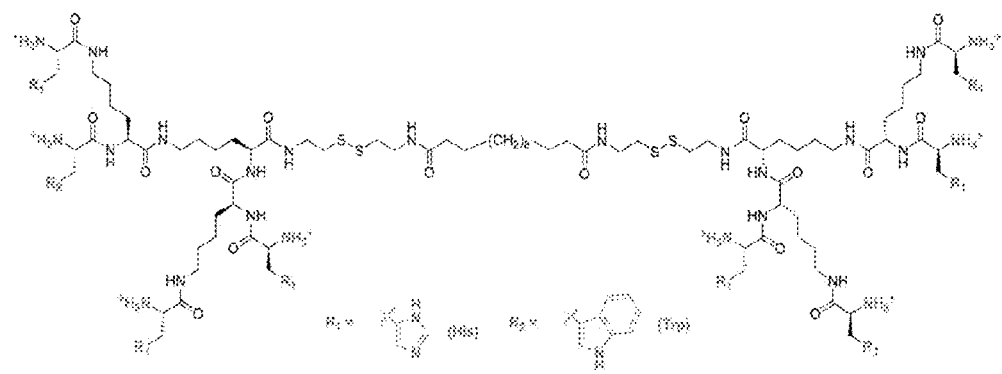

FIG. 4 provides an alternate embodiment of a His-Trp functionalized bolaamphiphile of the disclosure, F10-G2-75H25W.

Figure 5:
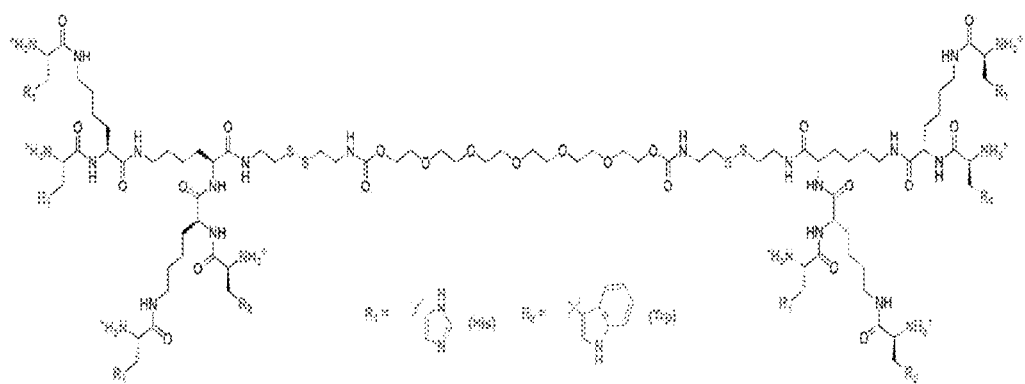

FIG. 5 provides yet another alternate embodiment of a His-Trp functionalized bolaamphiphile of the disclosure, HEG-G2-75H25W.

Figure 6:
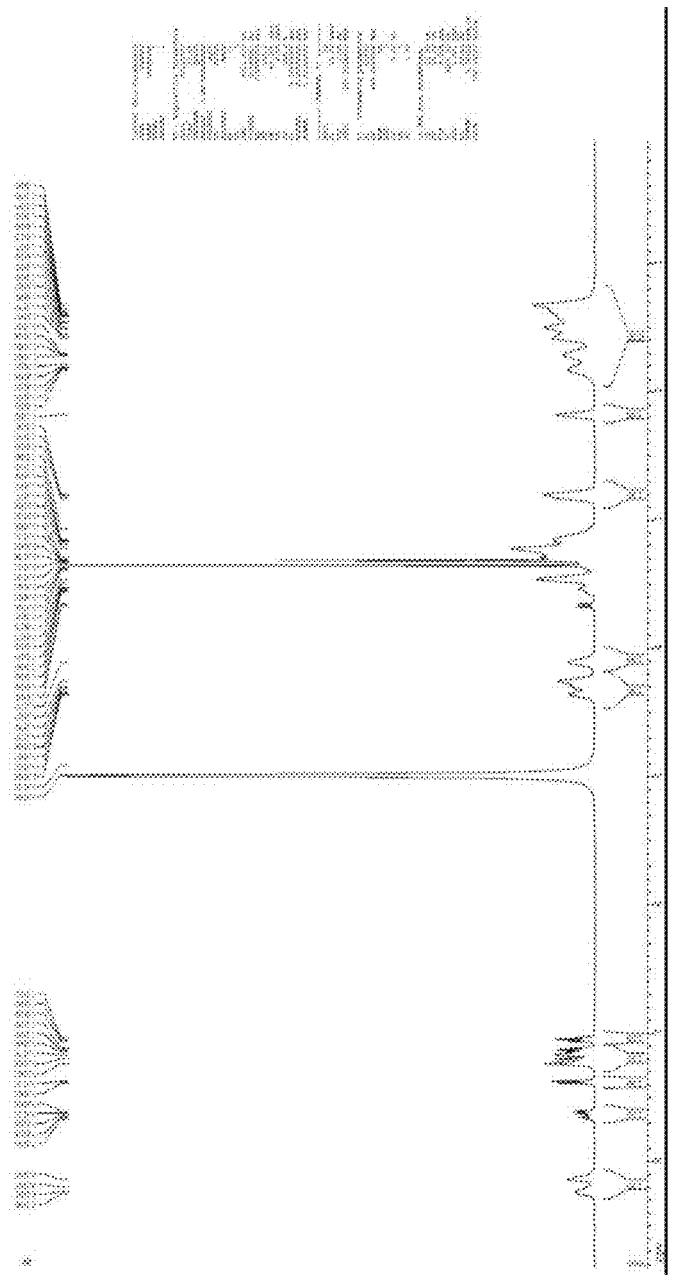

FIG. 6 provides a $^1$H NMR spectrum for bola-C6-G2.

Figure 7:
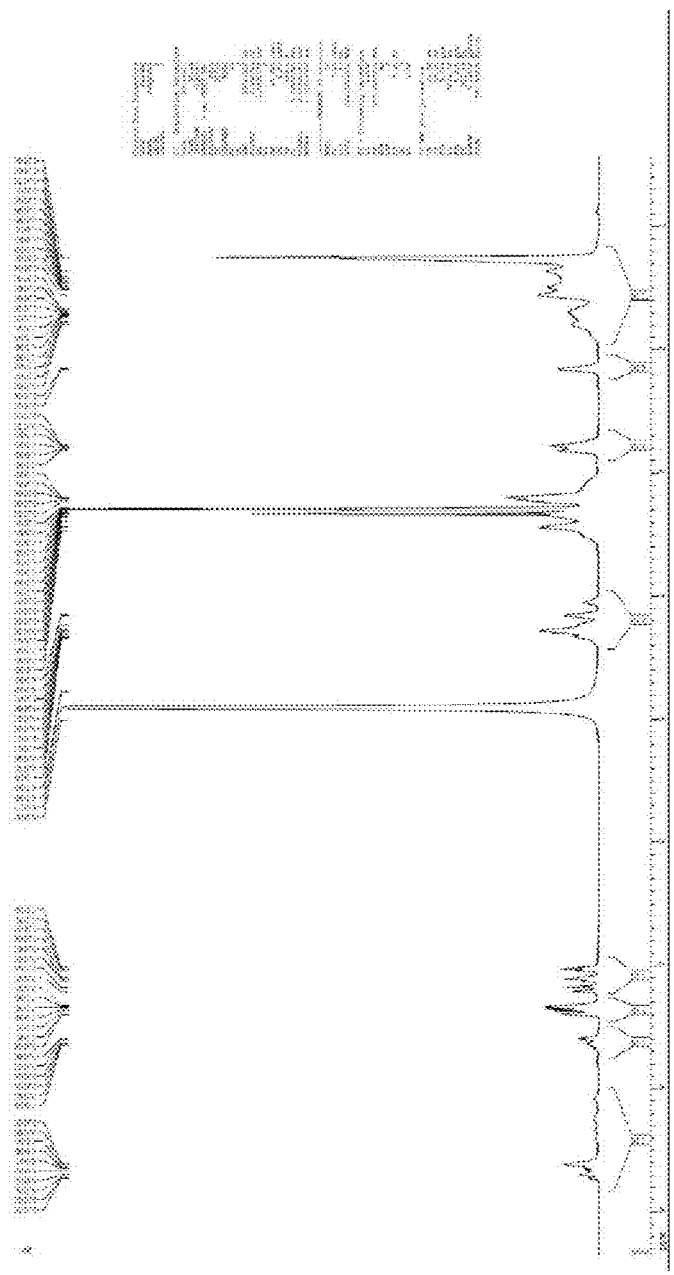

FIG. 7 provides a $^1$H NMR spectrum for bola-C18-G2.

Figure 8:
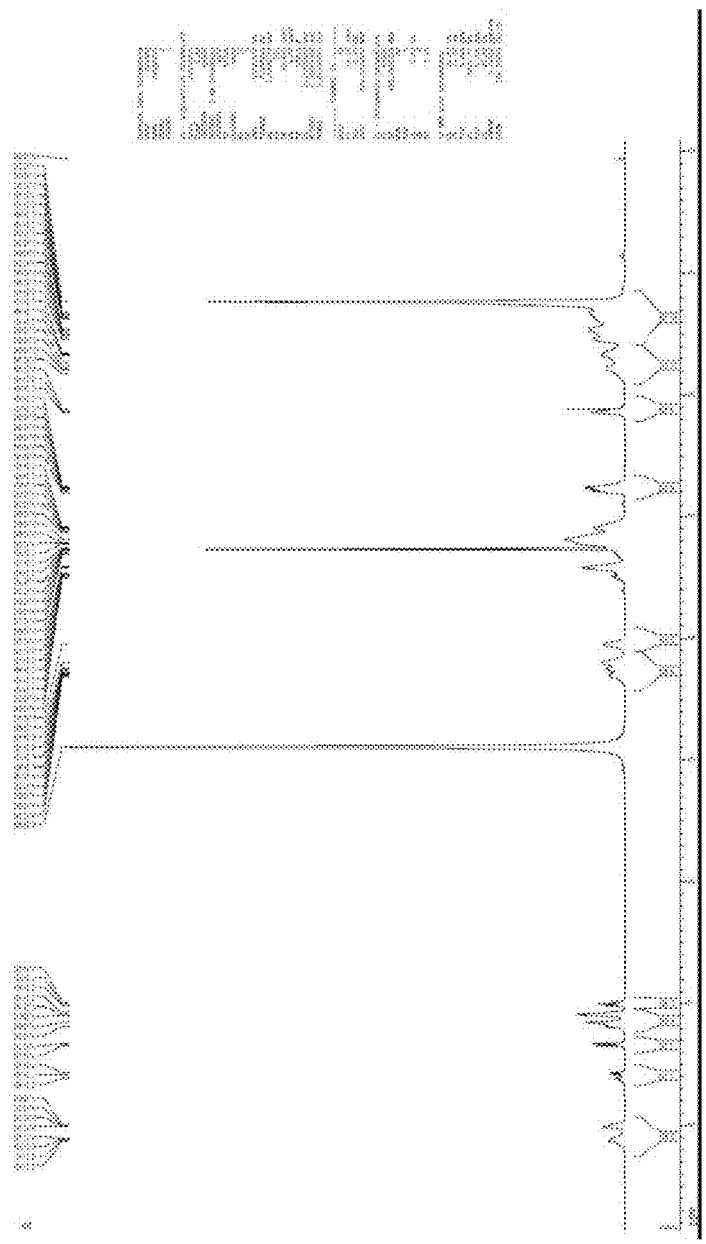

FIG. 8 provides a $^1$H NMR spectrum for bola-C22-G2.

Figure 9:
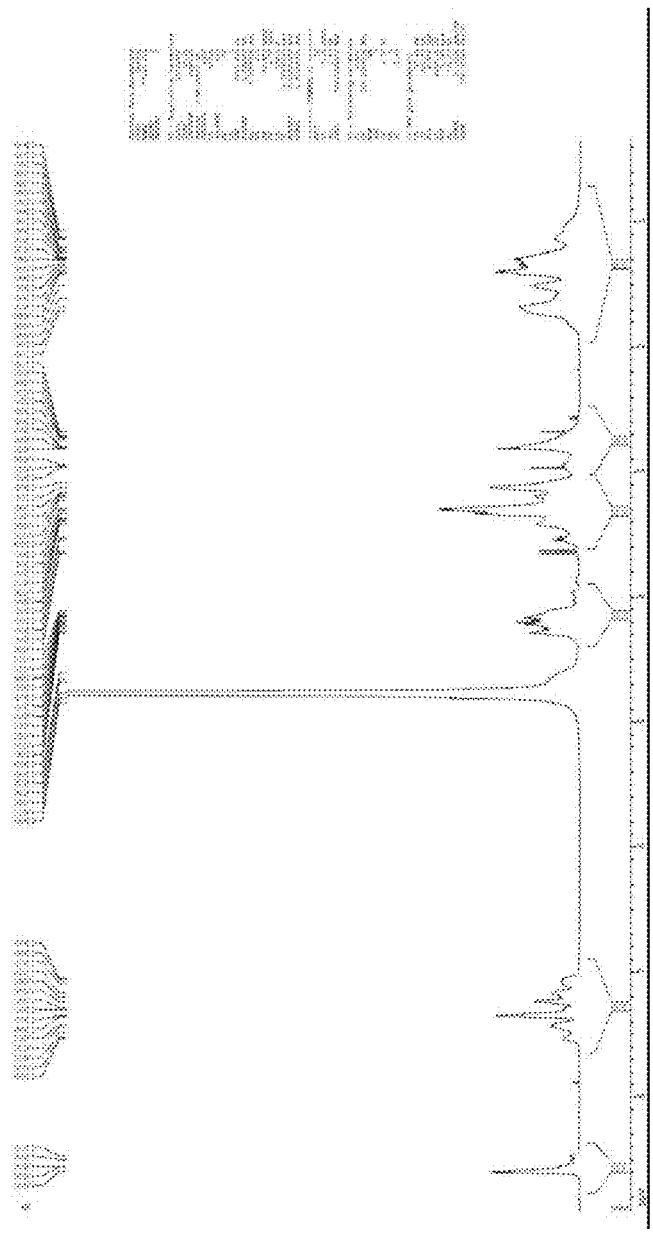

FIG. 9 provides a $^1$H NMR spectrum for bola-F8-G2.

Figure 10:
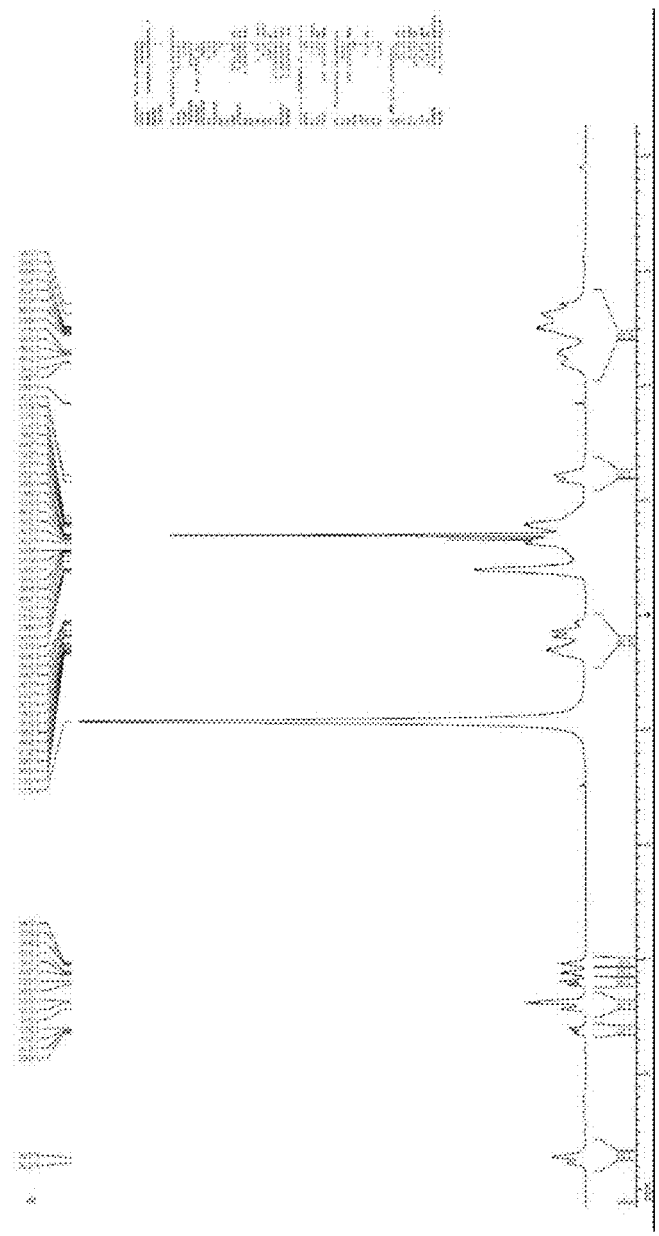

FIG. 10 provides a $^1$H NMR spectrum for bola-HEG-G2.

FIG. 11A-H presents transmission electron microscope (TEM) images of different amphiphile complexes. (A) m-C11-G2; (B) m-OA-G2; (C) bola-1,4-TZ-G2; (D) bola-1,5-TZ-G2; (E) bola-F10-G1; (F) bola-F10-G2; (G) bola-F10-G3; and (H) m-OA2-G2.

FIG. 12 presents infrared (IR) spectra of different bolaamphiphile complexes. All complexes were prepared at N/P=10 and 20 mM siRNA concentration.

Figure 13:
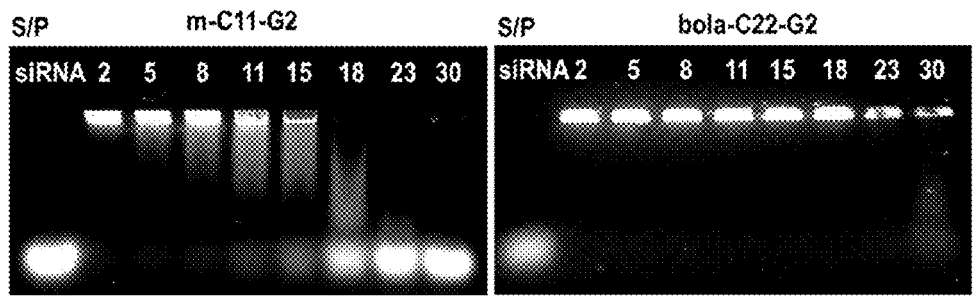

FIG. 13 provides a dextran sulfate competitive binding assay of mono and bola amphiphile complexes. m-C11-G2 and bola-C22-G2 were chosen for comparison as they have exactly the same ratio of hydrophilic to hydrophobic groups.

Figure 14:
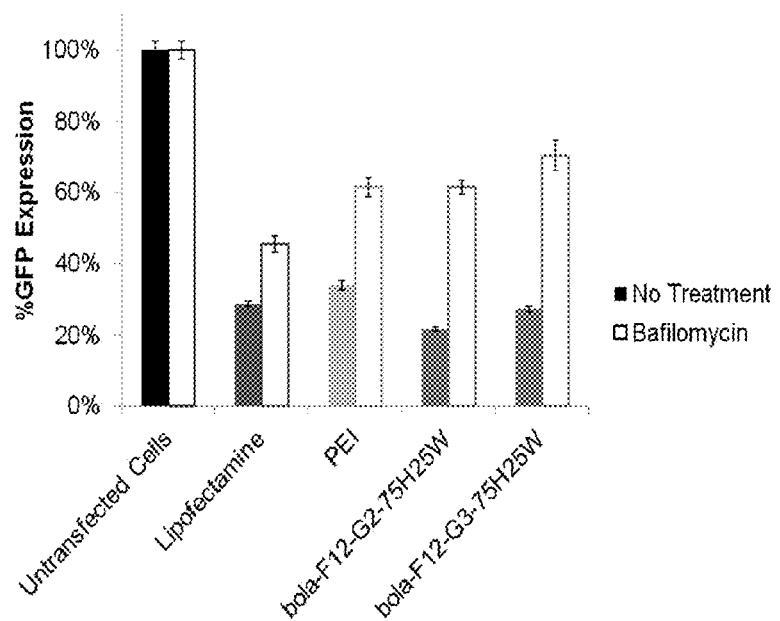

FIG. 14 demonstrates that bolaamphiphile transfection efficiency was inhibited by Bafilomycin.

FIG. 15A-C provides graphs demonstrating the concentration dependent inhibition of cell uptake. (A) siRNA-Cy3 uptake was quantified by the mean Cy3 fluorescence of each cell; cells were transfected with polyethylenimine alone (left), with bola-F10-G2-75H25W (center), or with bola-F10-G3-75H25W; cells were treated without or with increasing concentrations of chlorpromazine, an inhibitor of clathrin-mediated endocytosis; (B) siRNA-Cy3 uptake was quantified by the mean Cy3 fluorescence of each cell; cells were transfected with polyethylenimine alone (left), with bola-F10-G2-75H25W (center), or with bola-F10-G3-75H25W; cells were treated without or with increasing concentrations of genistein, an inhibitor of caveolar endocytosis; and (C) Cy3-labeled siRNA was complexed with FITC-labeled amphiphiles at N/P 45; cells were transfected with FITC-dextran alone (left), with bola-F10-G2-75H25W (center), or with bola-F10-G3-75H25W; cells were treated without or with increasing concentrations of EIPA, an inhibitor of macropinocytosis.

FIG. 16A-B provides for the hemolysis and toxicity of different peptide amphiphiles and bolaamphiphiles. (A) Bovine red blood cells (RBCs) were treated with different amphiphiles and bolaamphiphile and the absorption (A540 nm) of the supernatant was measured as an indicator of hemolysis. Percent hemolysis was calculated by comparing the sample with negative control (PBS) and positive control (10 mg/mL Triton X-100). (B) Cytotoxicity of different amphiphiles and bolaamphiphiles to NIH 3T3 cells as determined by an MTT assay.

FIG. 17A-L provides for the controlled self-assembly of bolaamphiphiles with siRNA. (A) Schematic illustration of bolaamphiphile (bola) and siRNA self-assembly. (B)-(D) TEM images of C18 bolas complexes with headgroups at different generations. Scale bar: 100 nm. (E)-(G) Proposed self-assembly structures of different bola complexes. (H) DLS measurement of different bola complexes. (I) Triggered siRNA release by reducing reagent glutathione (GSH). Different bola-G2 complexes (named by the core) were treated with (+) GSH or PBS (−) before gel electrophoresis. (J)-(L) Dextran sulfate competitive binding assay with different bola complexes.

FIG. 18A-N shows Cy-3 siRNA complexed with different amphiphiles and bolaamphiphiles (bolas) that were transfected into NIH 3T3 cells. (A)-(D) Confocal fluorescence images of transfected cells (cell nuclei were counter-stained with DPAI, scale bar: 20 μm). (E) and (F) Cell uptake of different mono and bola amphiphiles quantified by flow cytometry. (G)-(I) Comparison of cell uptake mediated by vesicular complexes and micellar complexes. (J)-(N) Cellular uptake of bola complexes after energy depletion. (J)-(K) Transfection of Cy3-siRNA complexes carried out at 37° C. or 4° C. for 4 h. (L) 3T3 cells were treated by sodium azide ($NaN_3$) and 2-Deoxy-D-glucose (DG) for 1 hour prior to transfection. (M)-(N) provides figures in regards to the endocytotic pathway of bola complexes. 3T3 cells were treated with chlorpromazine (30 μM), genistein (350 μM), or EIPA (30 μM) for 1 hour prior to transfection of Cy3-siRNA/bola complexes.

FIG. 19A-C presents a transfection summary and cell uptake mechanism. (A) and (B), transfection summary of mono and bola amphiphiles. NIH 3T3 cells with stable GFP expression were transfected with different anti-GFP siRNA complexes, mean GFP fluorescence of each cell was analyzed by flow cytometry after transfection. (C) Dose-response curve of different bola complexes.

Figure 20A:
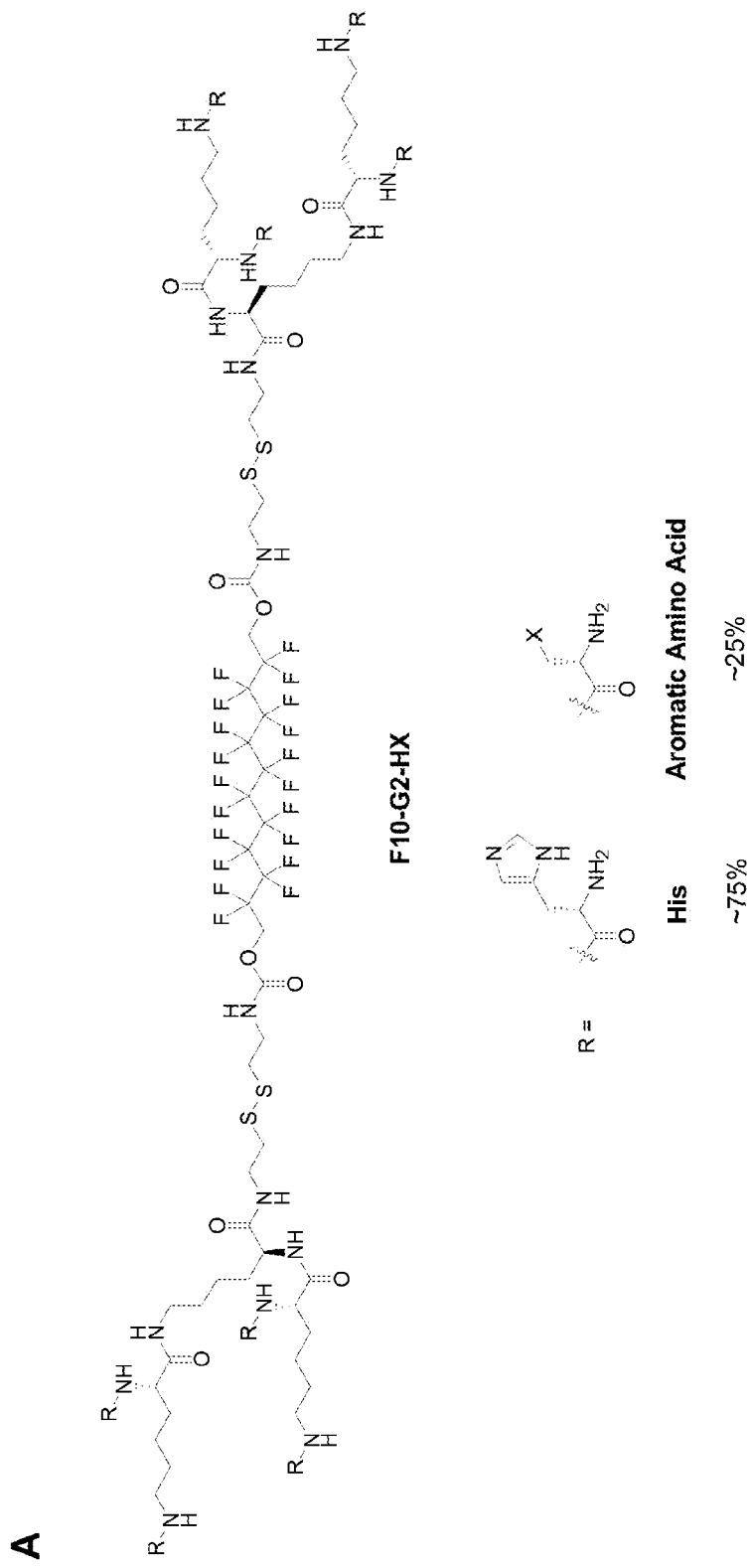
Figure 20B:
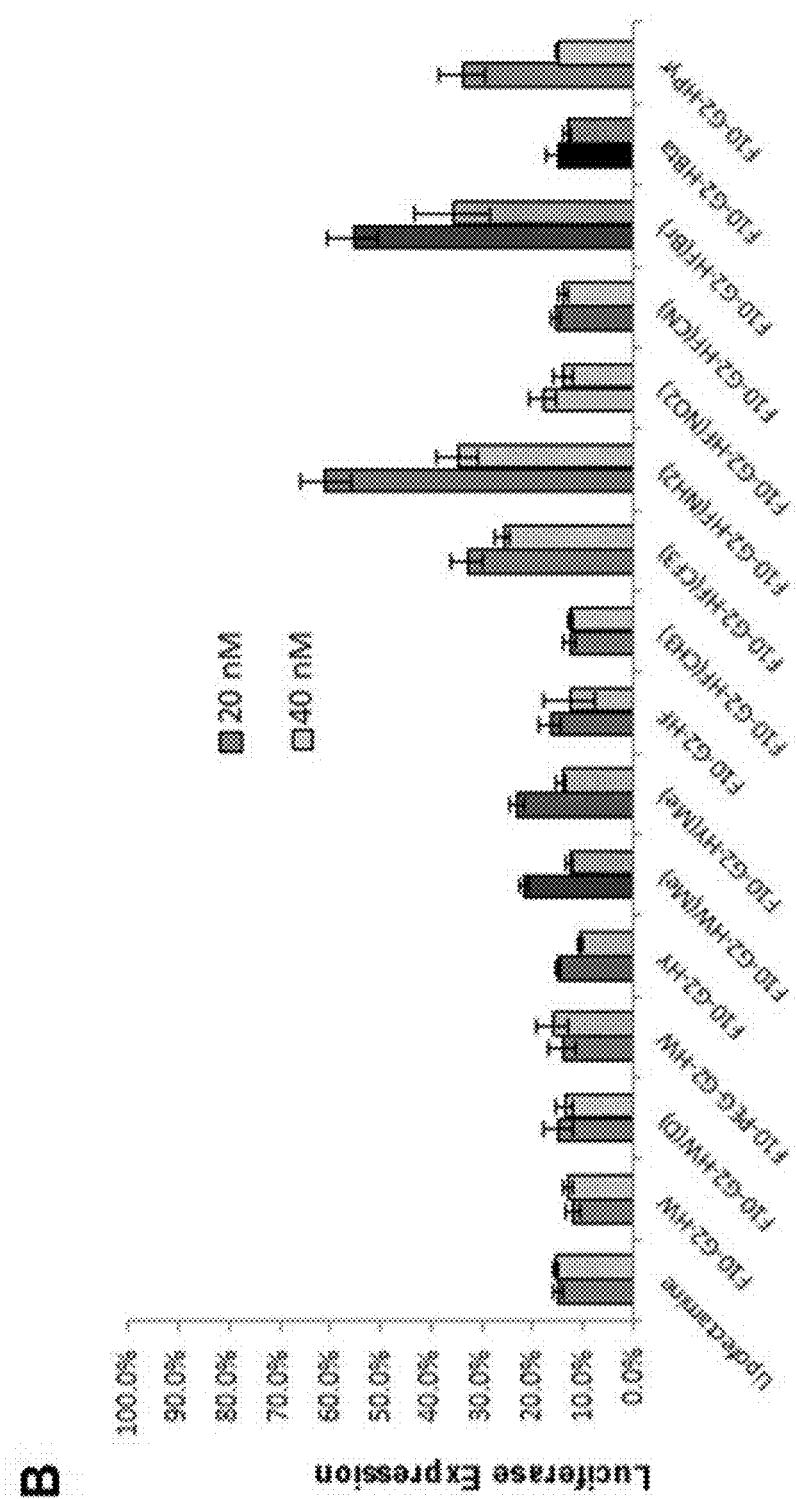

FIG. 20A-C provides for (A) bolaamphiphiles comprising a fluorinated hydrophobic core and dendrons comprised of histidine and various natural occurring and nonnaturally occurring aromatic amino acids (F10-G2 aromatic variants). (B) Transfection screening of F10-G2 aromatic variants in MDA-MB-231-Luc Cells. [siRNA]=20 or 40 nM, N/P=45, samples were prepared in OptiMEM. (C) Provides examples of natural occurring and nonnaturally occurring aromatic amino acids.

FIG. 21A-C provides studies looking at improving transfection efficiencies by increasing bollamphiphile colloidal stabilities by PEGylation. (A) Shows a scheme to co-formulate fluorocarbon bollamphiphiles with PEG (fPEG2K) using a one-pot synthesis reaction with p-nitro chloroformate. (B) Transfection screening with 0%, 1% or 10% fPEG with F10-G2 aromatic variants in MDA-MB-231-Luc Cells. [siRNA]=10 or 20 nM, N/P=40 unless otherwise noted, samples were prepared in OptiMEM. (C) DLS studies conducted at multiple time points with 0%, 1% or 10% fPEG. F10-G2-H/W and fPEG2k were mixed in ethanol, the solvent was removed in vacuo, and the thin film was dissolved in dd$H_2O$. The complexes were prepared in low-salt PBS (N/P=30) and then diluted into high-salt PBS (10 mM phosphate, pH=7.4, 100 mM NaCl) prior to DLS.

DETAILED DESCRIPTION

As used herein and in the appended claims, the singular forms "a," "an," and "the" include plural referents unless the context clearly dictates otherwise. Thus, for example, reference to "a siRNA" includes a plurality of such siRNAs and reference to "the bolaamphiphile" includes reference to one or more bolaamphiphile and equivalents thereof known to those skilled in the art, and so forth.

Unless defined otherwise, all technical and scientific terms used herein have the same meaning as commonly understood to one of ordinary skill in the art. Although many methods and reagents similar or equivalent to those described herein, the exemplary methods and materials are presented herein.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise. In certain embodiments, an alkenyl may be substituted with fluorine atoms.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise. In certain embodiments, an alkyl may be substituted with fluorine atoms.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise. In certain embodiments, an alkynyl may be substituted with fluorine atoms.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. In certain embodiments, an aryl may be substituted with fluorine atoms.

The term "aromatic amino acid", as used in this disclosure, refers to molecules which are composed of amine and carboxylic acid functional groups, along with side chains that comprise aryl or heteroaryl groups. Examples of aromatic amino acids, include the naturally occurring aromatic amino acids, such as L-tyrosine, L-phenylalanine, L-tryptophan, and L-Dopa; and non-naturally occurring amino acids, such as D-tyrosine, D-phenylalanine, and D-tryptophan. Additional examples of aromatic amino acids include, those having the structures presented in FIG. 20C. It is further contemplated, that any of the structures presented in FIG. 20C may be further substituted with additional functional groups at the same or different ring positions. Such amino acids would be also be considered as "aromatic amino acids" for this disclosure.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof. In certain embodiments, a cycloalkenyl may be substituted with fluorine atoms.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof. In certain embodiments, a cycloalkyl may be substituted with fluorine atoms.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "heterocycle", as used in this disclosure, refers to ring structures that contain at least 1 noncarbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. In certain embodiments, a heterocycle may be substituted with fluorine atoms. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "substituent" refers to an atom or group of atoms substituted in place of a hydrogen atom. For purposes of this disclosure, a substituent would include deuterium atoms.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

RNA interference (RNAi) presents a tremendous potential for disease treatment. However, the delivery of small interfering RNA (siRNA), the molecule that mediates RNAi, into cells still poses great challenge. Considerable effort has been directed to the development of safe and effective delivery vectors. To date, cationic lipid mediated transfections are the most advanced techniques used to deliver siRNA in the pre-clinical setting. These lipids were generally co-formulated with different functional components to form stable lipid nanoparticle with siRNA, and have demonstrated successful in vivo delivery in several animal models. Highly efficient lipid structures were mostly discovered through combinatorial synthesis and high throughput screening. A clear relationship between the molecular structure and biological activity has not yet been determined. The lack of structure-activity relationship (SAR) information greatly hinders the understanding of delivery systems as well as impeding rational design for new vectors. Furthermore, despite the current success of lipid-based delivery, the amphiphilic lipid structure interrupts cell membranes and potentially raises safety concerns. Therefore, vectors for safe and effective siRNA delivery are still highly desirable for a broader application of RNAi.

The ability to deliver certain bioactive agents to the interior of cells is problematical due to the bioavailability restriction imposed by the cell membrane. The plasma membrane of the cell forms a barrier that restricts the intracellular uptake of molecules to those which are sufficiently non-polar and smaller than approximately 500 daltons in size. Previous efforts to enhance the cellular internalization of proteins have focused on fusing proteins with receptor ligands or by packaging them into caged liposomal carriers. However, these techniques often result in poor cellular uptake and intracellular sequestration into the endocytic pathway.

Other highly charged nucleic acid molecules with therapeutic potential face the same delivery barrier. For example, RNA aptamers have great potential to bind to, sequester and inhibit proteins, but at >10,000 Daltons and highly charged, they have no or limited ability to enter cells on their own. The methods and compositions of the disclosure allow for intracellular delivery of RNA aptamers, siRNA and DNA vectors.

Due to their anionic charge and large size of ~14,000 Daltons, delivery of siRNA is a formidable challenge in mammals, including humans. The disclosure provides methods and compositions to facilitate and improve cellular uptake of nucleic acid molecules by using a peptide bolaamphiphile-based vector system.

The disclosure provides compositions and methods for the delivery of sequence specific oligonucleotides or polynucleotides useful to selectively treat human diseases and to promote research. The compositions and methods of the disclosure can effectively deliver oligonucleotides and polynucleotides, including siRNAs, RNA aptamers, and DNA vectors to subjects, including the cells of the subjects. The disclosure overcomes size and charge limitations that make oligonucleotides and polynucleotides difficult to deliver. By using a compound of the disclosure, nucleic acids can be encapsulated and effectively delivered into a cell in vitro and in vivo with minimal toxicity.

The disclosure provides for a rationally designed peptide bolaamphiphile (termed as "bola" in this disclosure) structure for nucleic acid delivery. Unlike regular lipid-like amphiphiles (termed as "mono amphiphile" in this disclosure), which are composed of one or multiple hydrophobic tails on one side and one hydrophilic headgroup on the other (e.g., see FIG. 1A), bolas are composed of two hydrophilic headgroups on both ends connected via a hydrophobic core (e.g., see FIG. 1B). Bola structures were first characterized from the unique cell membranes of archaebacteria. The mono layer membrane formed by bolas provides superior stability than regular lipid bilayer membranes, and helps archaebacteria survive in extreme conditions.

The disclosure provides for innovative compounds that form stable nucleic acid-encapsulating nanoparticles (e.g., siRNA-encapsulating nanoparticles). The resulting nucleic acid-encapsulating nanoparticles are more stable than conventional lipids, providing for better delivery of nucleic acids into cells. Due to bolas unique molecular structure, it was postulated that the compound disclosed herein would not insert into a lipid bilayer membrane thereby presenting a more biocompatible alternative to cationic lipids. The disclosure provides for a rationally designed peptide bolaamphphile system that can deliver nucleic acids more efficiently than other related vector systems with less toxicity.

Lipid-like mono amphiphiles (i.e., cationic lipids) can disrupt cell membranes because of structural similarity. Cationic headgroups can be easily attracted to negatively charged phospholipids, that is then followed by insertion of hydrophobic tail into the lipid bilayer (e.g., see FIG. 1D). Such interactions induce lipid phase transition from lamellar to hexagonal, causing membrane disruption and cytotoxicity. To avoid such detrimental effects, the compounds disclosed herein were designed to meet two criteria: (A) have large headgroups to avoid a U-shaped conformation for membrane insertion; and (B) provide short hydrophobic core to prevent insertion across the cell membrane (e.g., see FIG. 1B). Based upon these criteria, a multifunctional peptide dendron was chosen as headgroups for the compounds disclosed herein (e.g., see FIG. 1C). The well-defined dendron provides a hyper-branched structure for multivalent interaction, and the size could be easily controlled through different dendron generations. A peptide-based dendron gives further benefits of biodegradability and biocompatibility. It was found that lysine-based dendronized polymers with histidine and aromatic amino acid functionalization on the outer layer produced good siRNA transfection efficiency with low cytotoxicity. Aromatic amino acids (naturally occurring or nonnaturally occurring) were found to improve siRNA binding by intercalation and helped cell uptake through membrane anchoring, while histidine facilitated endosomal escape by its good buffering capacity. In a particular embodiment, the compound disclosed herein comprises a lysine-based dendron functionalized with a certain molar percentage of histidine to aromatic amino acids as headgroups. For example, the molar percentage of histidine to aromatic amino acid (aaa) functionalization can be 90 mol % his to 10 mol % aaa; 85 mol % his to 15 mol % aaa; 80 mol % his to 20 mol % aaa; 75 mol % his to 25 mol % aaa; 70 mol % his to 30 mol % aaa; 65 mol % his to 35 mol % aaa; 60 mol % his to 40 mol % aaa; 55 mol % his to 45 mol % aaa; 50 mol % his to 50 mol % aaa; 45 mol % his to 55 mol % aaa; 40 mol % his to 60 mol % aaa; 35 mol % his to 65 mol % aaa; 30 mol % his to 70 mol % aaa; 25 mol % his to 75 mol % aaa; 20 mol % his to 80 mol % aaa; 15 mol % his to 85 mol % aaa; or 10 mol % his to 90 mol % aaa. The two headgroups can be attached to a central hydrophobic core, the core will promote self-assembly in an aqueous solution. In another embodiment, a bioreversible functional group was designed to connect the hydrophobic core and the headgroups that can be cleaved under the reducing environment in the cytoplasm or by enzymatic action, providing for stimuli-responsive disassembly of the peptide bolaamphiphile and facilitating nucleic acid release. For example, in a certain embodiment a disulfide linkage is provided that connects the hydrophobic core and the headgroups which can be cleaved under the reducing environment in the cytoplasm.

An embodiment of a compound disclosed herein is shown in FIG. 3E. In FIG. 3E and throughout the disclosure the molecule is named by the structure of the core and the generation of the dendron headgroups. For example, FIG. 3E provides for a bola-C18-G2 molecule. Due to the modular design of the compound disclosed herein, all three parts of the bola molecule could be modified for structure-property studies. For example, for the compound disclosed herein, different hydrophobic cores can be used, including long chain diacids (C6-C22) and fluorinated diols (F8 and F10), with the length of all cores significantly shorter than the width of a typical cell membrane. A hexa(ethylene glycol) core (HEG) was included as a hydrophilic control with no intramolecular attraction in aqueous solution. A triazole ring was also introduced to provide different geometry in the core, where 1,4-triazole (1,4-TZ) gives a more linear alkyl chain and 1,5-triazole (1,5-TZ) a kinked analog.

To study the effects of triggered release on nucleic acid (e.g., siRNA) transfection efficiency from a compound disclosed herein, a tri(ethylene glycol) linker (NR) was used as a non-reducible control. The size of the headgroup of the compound disclosed herein was varied from first to third generation (G1-G3). For a direct comparison between mono and bola amphiphiles, three mono amphiphile analogs were also designed with varying hydrophobic tails (e.g., see FIG. 1F). All molecules were synthesized by solution-phase coupling reactions, and detailed synthesis and characterization data can be found in the Examples section presented herein.

The compound of the disclosure in comparison to the conventional monoamphiphile structures of cationic lipids exhibited no membrane disruption and had limited cytotoxicity. Further, the compound disclosed herein could self-assemble with nucleic acids (e.g., siRNA) to form various nano-objects, and vesicular complexes. The compounds of the disclosure were found to have high siRNA transfection efficiency in vitro.

In comparison to other amphiphile systems, by directly controlling the molecular structure of the compound disclosed herein, the compound of the disclosure achieved dramatically improved self-assembly and bioactivity.

It is further envisioned that the compound of the disclosure could enable rational design of new biomaterials for a wider range applications.

In a further embodiment, a compound disclosed herein further comprises targeting ligands. Examples of targeting ligands, include but are not limited to, antibodies, aptamers, cholesterol and its derivatives, folate compounds or folate conjugates, transferrin, saccharides (e.g., mono-, di-, oligosaccharides), and cell-penetrating peptides. These targeting ligands can be conjugated to the dendronized polymers by using the techniques presented in Shu et al. (Annual Review of Physical Chemistry 64:631-657 (2013)), Gauthier et al. (Chem. Commun 23:2591-2611 (2008)), Menzel (*Advances in Polymer Science* 253:1-36 (2013)), Mero et al. (*Methods Mol Biol.* 751:95-129 (2011)), Roberts et al. (*Advanced Drug Delivery Reviews* 54:459-476 (2002)), Steenis et al. (*Journal of Controlled Release* 87:167-176 (2003)), which are incorporated herein in-full, including the references cited therein.

In another embodiment, a compound disclosed herein further comprises an oligonucleotide (e.g., siRNA) or a polynucleotide.

In a particular embodiment, the disclosure provides methods for delivering an oligonucleotide or polynucleotide to a cell in vitro or in vivo comprising contacting the cell with a compound disclosed herein. In a further embodiment, the disclosure provides methods for inducing an RNAi response in a cell by delivering a siRNA into a cell by using a compound disclosed herein.

As used herein, a nucleic acid domain, used interchangeably with oligonucleotide or polynucleotide domain can be any oligonucleotide or polynucleotide (e.g., a ribozyme, antisense molecule, siRNA, dsRNA, polynucleotide, oligonucleotide and the like). Oligonucleotides or polynucleotides generally contain phosphodiester bonds, although in some cases, nucleic acid analogs are included that may have alternate backbones, comprising, e.g., phosphoramidate, phosphorothioate, phosphorodithioate, or O-methyl-phophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments. Oligonucleotides, as used this disclosure, therefore encompass siRNAs which have been chemically modified to prolong the siRNA half-life in serum and increased cellular uptake. Examples of such modifications, including modifying the sugar moiety by incorporating a 2'-fluoro, 2'-omethyl, 2'-halogen, 2'-amine, or 2'-deoxy, or by bridging the sugar's 2' and 4' positions with a —O—CH$_2$ linker (i.e., a 'locked nucleic acid'); by modifying the internucleotide phosphate linkage in siRNA by replacing the phosphodiester linkage with phosphothioate or boranophosphate; by modifying the siRNA nucleobases by replacing uridine bases with 4-thiouridine, 5-bromouridine, 5-iodouridine, N-3-Me-uridine or 2,6-diaminopurine residues, or by replacing seed region nucleotides 2-8 (from the 5'end of the guide strand) of siRNA with DNA nucleotides. Mixtures of naturally occurring nucleic acids and analogs are encompassed by the term oligonucleotide and polynucleotide; alternatively, mixtures of different nucleic acid analogs, and mixtures of naturally occurring nucleic acids and analogs can be made. Furthermore, hybrids of DNA and RNA can be used. dsDNA, ssDNA, dsRNA, siRNA are encompassed by the term oligonucleotide and polynucleotide. Additionally, the term oligonucleotides and polynucleotides, as used herein, includes modifications of siRNA termini, including tagging the ends of siRNAs with moieties such as cholesterol, folate, various peptides, and aptamers; fluorescent molecules; 3'-biotin; and 3'-ends with dinucleotide overhangs that mimic Dicer cleavage products.

A polynucleotide refers to a polymeric compound made up of any number of covalently bonded nucleotide monomers, including nucleic acid molecules such as DNA and RNA molecules, including single- double- and triple-stranded such molecules, and is expressly intended to embrace that group of polynucleotides commonly referred to as "oligonucleotides", which are typically distinguished as having a relatively small number (no more than about 30, e.g., about 5-10, 10-20, and 20-30) of nucleotide bases.

As used herein, the term "siRNA" is an abbreviation for "short interfering RNA", also sometimes known as "small interfering RNA" or "silencing RNA", and refers to a class of nucleotide-long double-stranded ribonucleic acid molecules that in eukaryotes are involved in the RNA interference (RNAi) pathway that results in post-transcriptional, sequence-specific gene silencing.

The term "dsRNA" is an abbreviation for "double-stranded RNA" and as used herein refers to a ribonucleic acid molecule having two complementary RNA strands.

As described above, the nucleic acid may be DNA, both genomic and cDNA, RNA or a hybrid, where the nucleic acid may contain combinations of deoxyribo- and ribonucleotides, and combinations of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

The nucleic acid domain of a nucleic acid construct described herein is not limited by any particular sequence. Any number of oligonucleotide or polynucleotides useful for diagnostics, therapeutics and research can be used in the methods and compositions of the disclosure.

The practice of phosphoramidite chemistry to prepare oligonucleotides is known from the published work of M. Caruthers and S. Beaucage and others. U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference, describe methods of oligonucleotide synthesis. Additionally, the practice of phosphoramidite chemistry has been systematically reviewed by Beaucage and Iyer (*Tetrahedron* 48:2223-2311 (1942)) and (*Tetrahedron* 49:6123-6194 (1993)), or references referred to therein, all of which are herein incorporated by reference.

Nucleic acid synthesizers are commercially available and their use is generally understood by persons of ordinary skill in the art as being effective in generating nearly any oligonucleotide of reasonable length which may be desired.

In practicing phosphoramidite chemistry useful 5'OH sugar blocking groups are trityl, momomethoxytrityl, dimethoxytrityl and trimethoxytrityl, especially dimethoxytrityl (DMTr). In practicing phosphoramidite chemistry useful phosphite activating groups, i.e., NR$_2$, are dialkyl substituted nitrogen groups and nitrogen heterocycles. One approach includes the use of the di-isopropylamino activating group.

Oligonucleotides can be synthesized by a Mermade-6 solid phase automated oligonucleotide synthesizer or any commonly available automated oligonucleotide synthesizer. Triester, phosphoramidite, or hydrogen phosphonate coupling chemistries described in, for example, M. Caruthers, Oligonucleotides: Antisense Inhibitors of Gene Expression., pp. 7-24, J. S. Cohen, ed. (CRC Press, Inc. Boca Raton, Fla., 1989) or Oligonucleotide synthesis, a practical approach, Ed. M. J. Gait, IRL Press, 1984; "Oligonucleotides and Analogues, A Practical Approach", Ed. F. Eckstein, IRL Press, 1991, are employed by these synthesizers to provide the desired oligonucleotides. The Beaucage reagent, as described in, for example, *Journal of American Chemical Society* 112:1253-1255 (1990), or elemental sulfur, as described in Beaucage et al., (*Tetrahedron Letters* 22:1859-1862 (1981)), is used with phosphoramidite or hydrogen phosphonate chemistries to provide substituted phosphorothioate oligonucleotides. For example, the reagents comprising the protecting groups recited herein can be used in numerous applications where protection is desired. Such applications include, but are not limited to, both solid phase and solution phase, oligo-synthesis, polynucleotide synthesis and the like. The use of nucleoside and nucleotide analogs is also contemplated by this disclosure to provide oligonucleotide or oligonucleoside analogs bearing the protecting groups disclosed herein. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into an oligonucleotide or oligonucleoside sequence, they allow hybridization with a naturally occurring oligonucleotide sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

For instance, structural groups are optionally added to the ribose or base of a nucleoside for incorporation into an oligonucleotide, such as a methyl, propyl or allyl group at the 2'-0 position on the ribose, or a fluoro group which substitutes for the 2'-O group, or a bromo group on the ribonucleoside base. For use with phosphoramidite chemistry, various amidite reagents are commercially available, including 2'-deoxy amidites, 2'-O-methyl amidites and 2'-O-hydroxyl amidites. Any other means for such synthesis may also be employed. The actual synthesis of the oligonucleotides is well within the talents of those skilled in the art. Similar techniques could also be used to prepare other oligonucleotides such as the phosphorothioates, methyl phosphonates and alkylated derivatives. Similar techniques and commercially available modified amidites and controlled-pore glass (CPG) products such as biotin, Cy3, fluorescein, acridine or psoralen-modified amidites and/or CPG (available from Glen Research, Sterling Va.) can also be used to synthesize fluorescently labeled, biotinylated or other conjugated oligonucleotides.

In other embodiments, the compound disclosed herein can be used for the safe and effective delivery of peptides, proteins, and therapeutic agents across biological membranes. For example, the peptide-based bolas of the disclosure provide for the effective delivery nucleotide or nucleoside therapeutics across biological membranes. Such nucleotide or nucleoside therapeutics, include but are not limited to, deoxyadenosine analogues, such as didanosine, vidarabine, pentostatin and cladribine; adenosine analogs, such as BCX4430; deoxycytidine analogues, such as cytarabine, emtricitabine, lamivudine, and zalcitabine; guanosine and deoxyguanosine analogs, such as abacavir, acyclovir, granciclovir and entecavir; thymidine and deoxythymidine analogues, such as stavudine, telbivudine, zidovudine; doxyuridine analogues, such as idoxuridine and trifluridine; and nucleobase and nucleotide analogs, such as 5-fluorouracil, allopurinol, oxypurinal, tisopurine, azathioprine, thioguanine fludarabine; and nucleotide analogues. Accordingly, the compounds of the disclosure can be used treat a variety of disorders and diseases that are amendable to treatment with nucleotide, nucleobase or nucleoside therapeutics.

In alternate embodiments, the compound disclosed herein can be used for the safe and effective delivery of peptides and proteins across biological membranes. Examples of such peptides and proteins, includes but is not limited to, cytokines and growth factors (e.g., TNF, GDNF, NGF, interleukins, retinoic acid, TGF, testosterone, estrogen, etc.), peptide therapeutic agents (e.g., glucagon-like peptide-1 (GLP-1) agonists, teduglutide, pasireotide, exenatide, liraglutide, lixisenatide, albiglutide, glucose-dependent insulinotropic peptide, glucagon-like peptide 2, cyclosporine, and desmopressin), insulin and insulin analogs. Accordingly, the compounds of the disclosure can be used treat a variety of disorders and diseases that are amendable to treatment with peptide or protein therapeutics.

In a certain embodiment, the disclosure provides for a pharmaceutical composition which comprises the compound of the disclosure and one or more pharmaceutically acceptable agents, such as excipients, diluents, auxiliaries, carriers, etc. Moreover, the pharmaceutical composition can be formulated into a form suitable for administration to a subject including the use of carriers, excipients, additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The pharmaceutical compositions according to the disclosure may be administered at a therapeutically effective amount either locally or systemically. As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regime can be adjusted to provide the optimum therapeutic response. For example, several divided doses can be administered daily or the dose can be proportionally reduced as indicated by the exigencies of the therapeutic situation.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic in the amounts employed. In addition, the pharmaceutical composition can be incorporated into sustained-release preparations and formulations.

In some embodiments, pharmaceutical compositions comprising the compounds disclosed herein can be used to locally administer siRNA and antisense oligonucleotides. For example, such oligonucleotide-based therapeutics can be locally administered into the eyes for eye-related disorders. Because oligonucleotides are directly injected into the eye, the amount of material required is much smaller (and consequently less expensive) compared to that required for systemic drug delivery. Other advantages of targeting ocular tissue include lower RNase levels in the eye, compared to blood, and inherent host defense and clearance mechanisms that may promote cellular uptake of siRNA in the eye. Additionally, pharmaceutical compositions comprising the compounds can be used to locally deliver siRNA to the respiratory system, e.g., intranasal administration of synthetic siRNA. Such intranasal delivery, can allow for treatment of influenza and respiratory syncytial virus.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the subject to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent (e.g., siRNAs) as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The disclosure is illustrated in the following examples, which are provided by way of illustration and are not intended to be limiting.

EXAMPLES

Materials.

Unless otherwise noticed, all reagents were used as received from commercial suppliers without further purification. Protected amino acids were purchased from Advanced ChemTech (Loiusville, Ky.) and Aroz Technologies, LLC. (Cincinnati, Ohio). Coupling reagents were purchased from GL Biochem Ltd. (Shanghai, China). Branched polyethyleneimine (PEI, 25 kDa) was purchased from Sigma-Aldrich (St. Louis, Mo.). Sodium Dextran Sulfate (25 kDa) was purchased from TCI America (Portland, Oreg.) and was used as received. GelRed™ siRNA stain was purchased from VWR (Radnor, Pa.). Silencer anti-GFP siRNA, Silencer Select negative control siRNA, Silencer Cy™-3 labeled Negative Control siRNA and Lipofectamine RNAiMAX were purchased from Invitrogen (Carlsbad, Calif.). All reactions were performed in HPLC grade solvents unless otherwise noted. All water used in biological experiments was nanopure water obtained from Barnstead Nanopure Diamond (Waltham, Mass.). Ultrathin Carbon Type-A, 400 mesh TEM grids were purchased from TED PELLA Inc. (Redding, Calif.) Unmodified NIH 3T3 cell and engineered NIH 3T3 cell expressing enhanced green fluorescent protein (GFP) were a generous gift from Professor Young Jik Kwon (Department of Chemical Engineering, UC Irvine, Calif.). 100% bovine red blood cells suspension was purchased from Lampire Biological Laboratories (Pipersville, Pa.). Cell culture media, Dulbecco's modified Eagle's medium (DMEM) and fetal bovine serum (FBS) were purchased from Invitrogen (Carlsbad, Calif.).

Instruments.

All compounds were characterized by NMR and MS. $^1$H NMR spectra were recorded at 500 MHz on Bruker instruments. $^1$H NMR chemical shifts were reported as values in ppm relative to specified deuterated solvents. The size and zeta potential of bola/siRNA complexes were measured at 633 nm using Zetasizer dynamic light scattering instrument (Malvern Instruments, Malvern, UK) at 25° C. with detection angle of 173°. TEM was performed on a FEI Tecnai G2 TF20 high resolution TEM (Electron Imaging Center for NanoMachines, UCLA) operated at an accelerating voltage of 200 kV. The flow cytometry data was obtained on a Becton-Dickinson LSR II flow cytometer (Sue & Bill Gross Stem Cell Research Center, UCI) with an argon ion excitation laser at 488 nm. Confocal fluorescence images were acquired using a Zeiss LSM 510 inverted laser-scanning confocal microscope (Sue & Bill Gross Stem Cell Research Center, UCI).

Figure 2:
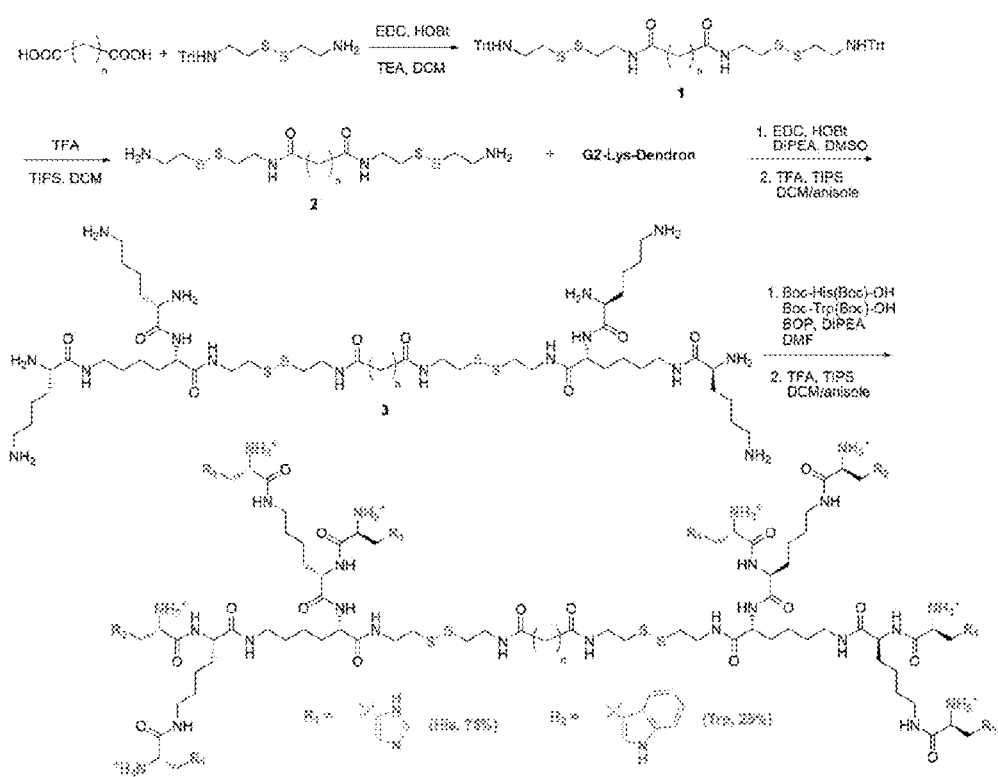

Peptide Bola Synthesis and Characterization According to the Scheme Presented in FIG. 2.

Synthesis of cystamine-terminated linker 1: Diacid (0.353 mmol, 1 equiv) and mono-trt protected cystamine (278.8 mg, 0.706 mmol, 2 equiv) were dissolved in 6 mL DCM in a round bottle flask, followed by the addition of DIPEA (135 μL, 0.777 mmol, 2.2 equiv), EDC.HCl (148.9 mg, 0.777 mmol, 2.2 equiv), and HOBt (105.0 mg, 0.777 mmol, 2.2 equiv). The reaction mixture was left to stir at ambient temperature overnight. After the reaction, the mixture was diluted with 150 mL DCM and washed with 0.02 N HCl in brine, 1.0 M NaHCO$_2$, and brine three times. The organic layer was dried over Na$_2$SO$_4$ and the solvent was removed in vacuo. The crude product was purified by column chromatography (1-3% TEA in DCM).

Deprotection of Trt-Protected Linker.

In a 15 mL round bottom flask, 1 (0.150 mmol) was dissolved in 4 mL DCM and 0.05 mL TIPS, followed by drop-wise addition of 0.5 mL TFA. The reaction was left to stir at ambient temperature for 1 hour, and all volatiles were removed in vacuo. The crude product was purified by re-dissolving in minimum DCM/MeOH mixture and precipitate in diethyl ether.

Synthesis of Lysine-Based Bolaamphiphile 3.

In a two-dram vial, 2 (0.0565 mmol, 1 equiv), boc-protected G2-Lysine-Dendron (90.7 mg, 0.113 mmol, 2 equiv) and DIPEA (21 μL, 0.120 mmol, 2.15 equiv) were dissolved in 2.5 mL DMSO, followed by the addition of EDC.HCl (23.0 mg, 0.120 mmol, 2.15 equiv), and HOBt (16.2 mg, 0.120 mmol, 2.15 equiv). The reaction was left to stir at ambient temperature for 24 h. After the reaction, the mixture was diluted with 150 mL DCM and washed with 0.02 N HCl in brine, 1.0 M NaHCO$_2$, and brine three times. The organic layer was dried over Na$_2$SO$_4$ and the solvent was removed in vacuo. The crude product was purified by dissolving in MeOH and precipitating in water. If necessary, the product was further purified by column chromatography (20~40% EtOAc in hexanes). After purification, Boc was deprotected in a de-protection mixture (typically, 1 mL TFA, 1.5 mL anisole, 2.5 mL DCM and 0.1 mL TIPS). The de-protection was done in 4 hours at ambient temperature, followed by solvent removal in vacuo. The product was then purified by re-dissolving in a minimal amount of MeOH and precipitating in Et$_2$O. The white precipitate was dissolved in nanopure water, filtered over a 0.22 μm filter and lyophilized to give 3 as a white powder.

Synthesis of His-Trp Functionalized Bola 4:

In a one drum glass vial were added 30 mg of unfunctionalized bola 3 (1 equiv), Boc-His(boc)-OH.DCHA (6 equiv) and Boc-Trp(boc)-OH (2 equiv). DMF (1.5 mL) was added to dissolve the solids, followed by BOP (8.2 equiv) and DIPEA (8.2 equiv). The reaction was left to stir for 24 hours at ambient temperature. Protected bola was precipitated in an excess amount of deionized water. After removing water completely, the solid was dissolved in 1 mL TFA, 2 mL DCM, 2 mL anisole and 0.25 mL TIPS. After stirring overnight, the solvent was removed in vacuo, the resulting solid was re-dissolved in MeOH and precipitated in Et$_2$O. The white precipitate was dissolved in water and lyophilized to give a white powder.

Characterization of Different Bolas by $^1$H NMR.

The functionalization ratio was determined by comparison of the characteristic aromatic peaks of imidazole (histidine) and indole (trytophan) ring.

C6-G2-75H25W: (see FIG. 2 for the structure and FIG. 6 for the spectrum)$^1$H NMR (d$^4$-MeOH): δ 8.25-8.14 (6.0H, histidine, 75 mol %), 7.65 (2.0H, tryptophan, 25 mol %), 7.38 (2H, tryptophan, 25 mol %), 7.23-7.06 (10H), 7.03 (2H, tryptophan, 25 mol %), 4.36-4.25 (10H), 4.11 (4H), 3.67-3.07 (multiple peaks overlapped with solvent peak, integration not accurate), 2.81 (8H), 2.17 (2H), 1.83-1.32 (44H).

C12-G2-75H25W: (see FIG. 2 for the structure) $^1$H NMR (d$^4$-MeOH): δ 8.25-8.14 (5.8H, histidine, 72 mol %), 7.65 (2.0H, tryptophan, 25 mol %), 7.38 (2.0H, tryptophan, 25 mol %), 7.23-7.06 (10H), 7.03 (2.0H, tryptophan, 25 mol %), 4.36-4.25 (10H), 4.11 (4H), 3.67-3.07 (multiple peaks overlapped with solvent peak, integration not accurate), 2.81 (8H), 2.17 (2H), 1.83-1.32 (56H).

C18-G2-75H25W: (see FIG. 2 for the structure and FIG. 7 for the spectrum)$^1$H NMR (d$^4$-MeOH): δ 8.25-8.14 (5.56H, histidine, 70 mol %), 7.63 (2.24H, tryptophan, 28 mol %), 7.39-7.33 (8H), 7.20-7.01 (3.31H, tryptophan, 28 mol %), 4.36-4.25 (10H), 4.11 (4H), 3.67-3.07 (multiple peaks overlapped with solvent peak, integration not accurate), 2.81 (8H), 2.17 (2H), 1.88-1.25 (68H).

C22-G2-75H25W: (see FIG. 2 for the structure and FIG. 8 for the spectrum)$^1$H NMR (d$^4$-MeOH): δ 8.13-8.04 (6.40H, histidine, 80 mol %), 7.61 (1.98H, tryptophan, 25 mol %), 7.34 (1.98H, tryptophan, 25 mol %), 7.19-7.00 (10H), 6.98 (2.01H, tryptophan, 25 mol %), 4.36-4.25 (10H), 4.11 (4H), 3.67-3.07 (multiple peaks overlapped with solvent peak, integration not accurate), 2.81 (8H), 2.17 (2H), 1.88-1.25 (70H).

F10-G2-75H25W: (see FIG. 3 for the structure)$^1$H NMR (D$_2$O): δ 8.56-8.47 (5.0H, histidine, 62 mol %), 7.53-7.04

(14.2H, tryptophan, 23 mol %), 5.00-4.90 (multiple peaks overlapped with solvent peaks), 4.85-4.10 (14H), 3.67-2.67 (40H), 1.71-1.06 (36H).

HEG-G2-75H25W: (see FIG. 4 for the structure and FIG. 10 for the spectrum)$^1$H NMR (d[4]-MeOH): δ 8.77-8.72 (5.91H, histidine, 74 mol %), 7.63 (2.25H, tryptophan, 28 mol %), 7.43-7.35 (8H), 7.21 (2.36H, tryptophan, 30 mol %), 7.11 (2.30H, tryptophan, 29 mol %), 7.02 (2.28H, tryptophan, 28 mol %), 4.33-4.13 (18H), 3.67-3.07 (multiple peaks overlapped with solvent peak, integration not accurate), 1.80-1.27 (36H).

Cytotoxicity and Hemolysis Studies.

MTT Assay: NIH 3T3 fibroblast cells were seeded at a density of 5000 cells/well in 96-well plates 24 hour in advance. The culture media was changed from 100 μL DMEM with 10% fetal bovine serum (FBS) to 80 μL serum free DMEM immediately before performing the toxicity assay. A 20 μL PBS solution containing different amount of bolas was then added to each well, followed by a 4 hour incubation. The media was then changed back to DMEM with 10% FBS and cultured for another 48 hours. The media was replaced with 50 μL DMEM solution containing 0.5 mg/mL MTT, followed by 4 hour incubation at 37° C. DMSO (100 μL) was added to the solution to dissolve the formed fomazan and the plate was incubated in a shaker at 37° C. for 30 min. The MTT reading was obtained by using a plate reader (Abs 540 nm). As a positive control, cells were also treated with poly(ethylene imine) (PEI) at different concentration under the same conditions.

Hemolysis Assay.

The cell membrane disruption of different dendron amphiphiles were measured by a hemolysis assay. A 100% bovine red blood cell (RBC) suspension was washed with PBS buffer and collected by centrifugation (10 min, 800×g) three times before the assay. 20 μL of the RBC suspension was then mixed with 80 μL of a PBS solution containing different amount of amphiphiles, followed by a 1 hour incubation at 37° C. RBCs were collected by centrifugation (800×g) for 10 minutes and the absorbance of the supernatant was measured at 540 nm. Pure PBS buffer was used as a negative control and 10 mg/mL Triton X-100 solution as the positive control. Percent hemolysis was calculated by comparing the absorbance of the sample with Triton X-100.

TEM Studies.

Unless otherwise specified, all siRNA-amphiphile complexes for TEM studies were prepared at 8.0 μM siRNA concentration and N/P ratio of 10. In a typical procedure, a solution containing dendron amphiphiles (10 μL) was added to a siRNA solution containing 160 pmol negative control siRNA (10 μL). The solution was briefly vortexed and incubated at ambient temperature for 1-2 hours before imaging. TEM grids (Ultrathin Carbon Type-A, 400 mesh) were glow discharged before use. The sample solutions (8 μL) were placed on the grid and let stand for 1 min. The solution was blotted away with a filter paper, while 2% uranyl acetate (15 μL) was pipetted onto the grid from the other side. After 1 min, the staining process was repeated with 2% Uranyl Acetate (15 μL). The solution was completely removed using filter paper and the grid was left air dry for 10 min before being placed into the TEM machine. Images were obtained on a FEI Tecnai G2 TF20 high resolution TEM operated at an accelerating voltage of 200 kV.

siRNA Binding Study.

Gel Electrophoresis. The binding of siRNA to bola was studied by agarose gel electrophoresis. Both siRNA and bola were diluted with 10 mM phosphate buffer (pH 7.4). Different amounts of bola solutions (5 mg/mL) were added to a 4 μM siRNA solution (5.0 μL) to achieve different N/P ratios. The same buffer was added to adjust the final volume to 10.0 μL, followed by a 30 min incubation at ambient temperature. 6× gel loading dye (2.5 μL) was added to each sample and 10 μL of the mixture was loaded into each well of a 1% agarose gel containing 1× GelRed dye. The electrophoresis was run in TAE buffer at 60 V for 45 min. The gel was then visualized under a UV transilluminator.

Dextran Sulfate Competitive Binding Assay.

The binding strength of siRNA to bola was studied by a competitive binding assay with dextran sulfate (DS). To a 4 μM siRNA solution (5 μL) was added different bola solutions at N/P 40. The mixtures were incubated for 1 hour at ambient temperature. DS solution (1 μL) at different concentrations were added to the complex to achieve different S/P ratios (the molar ratio of sulfate groups from DS and phosphate groups from siRNA) and the mixture was then incubated for another 30 min. The samples were then subjected to agarose gel electrophoresis under the aforementioned condition.

Glutathione Triggered Release of siRNA from Bola Complexes.

To a 4 μM siRNA solution (5 μL) was added concentrated bola solution to achieve a N/P ratio of 40. The final volume was adjusted to 10 μL by adding phosphate buffer (pH 7.4). After a 1 hour incubation at ambient temperature, 55 mM glutathione (GSH) (1 μL) was added to the solution to achieve a 5 mM final concentration, which was then followed by a 30 min incubation at ambient temperature. All samples were then subjected to agarose gel electrophoresis under the aforementioned condition.

DLS Measurements.

The size and zeta potential of bola/siRNA polyplexes were measured at 633 nm using Zetasizer (NanoZS) dynamic light scattering instrument (Malvern Instruments, Malvern, UK) at 25° C. with detection angle of 173°. Both bola and siRNA were diluted in nanopure water. The bola solution (50 μL) was added to a 1.5 μM siRNA solution (50 μL) (N/P 40), followed by brief vortexing. After a 30 minute incubation at ambient temperature, a DLS measurement was taken. The solution was then diluted with PBS (600 μL), and subjected to a zeta-potential measurement. At least three measurements were taken for each sample and the mean values were reported.

Cell Uptake and Protein Knockdown.

Sample preparation. The complex solution for transfection was prepared by simply mixing the amphiphile solution with the siRNA solution. In a typical procedure, a 1.5 μM siRNA solution was prepared by diluting the stock solution with PBS buffer. Different amphiphile solutions were also diluted by PBS buffer to a final volume of 12.3 μL. The amphiphile solution (12.3 μL) was then added to the 1.5 μM siRNA solution (6.7 μL), followed by brief vortexing. The solution was further agitated on a shaker for 30 min before transfection. As a positive control, Lipofectamine RNAIMAX was complexed with the same amount of siRNA following the vender's manual.

Confocal Laser Scanning Microscopy.

Confocal laser scanning microscopy was used to observe the trafficking of labeled siRNA in the transfected cells.

Unmodified NIH 3T3 fibroblast cells were seeded at a density of 15000 cells/well on an 8-well chamber slide (Lab-Tek, Rochester, N.Y.) 24 hours prior to transfection. Cy3-labeled siRNA was complexed with FITC-labeled amphiphiles at N/P 45 and transfected into the cells under the aforementioned conditions. After transfection, the media was changed back to DMEM supplemented with 10% fetal bovine serum. Confocal fluorescence spectroscopy was performed at different time points after the transfection. The nucleus was counter-stained by DAPI (25 µg/mL) for 30 min prior to imaging. All confocal images were acquired using a Zeiss LSM 510 inverted laser-scanning confocal microscope. A 40× numerical aperture of 1.4 oil immersion planapochromat objective was used for all experiments. A 559 nm helium-neon laser, a SMD640 dichroic mirror, and a 575-620 nm band-pass barrier filter were used to obtain the images of Cy3-labeled siRNA. FITC fluorescence of labeled amphiphile was acquired using a 488 nm excitation light, a SDM560 dichroic mirror, and a 505-540 nm band-pass barrier filter. Images of DAPI-stained nuclei were acquired using a 780 nm two-photon excitation light, a 635 nm dichroic mirror, and a 655-755 nm band-pass barrier filter. The three fluorescent images were scanned separately and overlaid together with the differential interference contrast image (DIC). The cells were scanned as a z-stack of two-dimensional images (1024×1024 pixels) and an image cutting approximately through the middle of the cellular height was selected to present the intracellular siRNA localization.

Transfection and Flow Cytometry.

NIH 3T3 fibroblast cells were seeded at a density of 10,000 cells/well in 48-well plates 24 hours in advance. Prior to transfection, the media was replaced with a serum-free DMEM solution (80 µL). Different complex solutions (20 µL) were added to each well to make the final siRNA concentration 100 nM. After a 4 hour incubation, the media was changed back to DMEM supplemented with 10% fetal bovine serum (250 µL) and cultured for another 48 hours. Before the analysis, cells were released from each well by trypsin and harvested by centrifugation (5 min, 500×g). Fluorescence of transfected cells was measured on a Becton-Dickinson LSR II flow cytometer with argon ion excitation laser. For each sample, data representing 10,000 objects were collected as a list-mode file and analyzed using FACSDiva™ software (Becton Dickinson, version 6.1.3).

For cell uptake assay, fluorescently labeled negative control siRNA (siRNA-Cy3) was used and the uptake was quantified by the mean Cy3 fluorescence of each cell. For GFP knockdown assay, both targeting siRNA (GFP-siRNA) and non-targeting negative control siRNA (Neg-siRNA) were transfected and the transfection efficiency was calculated by comparing the mean GFP fluorescence of GFP-siRNA treated cells with Neg-siRNA treated cells.

Statistical Analysis.

All quantitative assay were performed in triplicates, data were expressed as mean±SEM.

Hemolysis Assays Looking at Membrane Interaction by Bolaamphophiles.

Bovine red blood cells (RBC) were treated with different amphiphiles, and the release of hemoglobin from RBC was measured as an indicator of membrane lytic activity. FIG. 16A shows that mono amphiphiles exhibit much higher hemolysis than bolas. The hydrophobic tail of mono amphiphiles significantly changes their hemolytic activity, as the longer OA amphiphile exhibited 4 times higher membrane lysis than the shorter C11 amphiphile. Double tailed $OA_2$ amphiphile shows higher hemolysis at lower concentration, but plateaued at higher concentration, possibly due to self-assembly at high concentration. On the other hand, all bolas exhibited very low hemolytic activity, with G2 and G3 inducing below 1% hemolysis and G1 ~3% hemolysis at 250 µg/mL. The higher hemolysis induced by G1 bola is likely the result of the effect of the small headgroup size, the small G1 dendron does not provide enough steric hindrance to prevent U-shaped morphology, which could still insert into the cell membrane (e.g., See FIG. 1D). It should be noted that the different hemolysis was not caused by the assembly behavior, as all the concentrations tested are well below the critical micelle concentration (CMC) for both mono amphiphiles (Except for m-$OA_2$-G2) and bolaamphiphiles.

The membrane lytic activity of different amphiphiles also correlates with their cytotoxicity. As shown in FIG. 16B, mono amphiphiles are about two orders of magnitude more toxic than the bola analogs. And poly(ethylene imine) (PEI), a commonly used siRNA delivery polymer, induces higher toxicity than both mono and bola amphiphiles, further confirming the safety of bolas for siRNA delivery.

Rational Design of Bolaamphophiles for Self-Assembly and Bioactivity.

The self-assembly of peptide amphipihiles and dendron amphiphiles is a highly active research area. These amphiphiles have been demonstrated to form various nano structures, and several of them have been used for biomaterial applications. The direct control of self-assembly behavior and subsequent bioactivity is highly desirable for designer materials. In the compounds disclosed herein, one of the aims was to achieve such control through molecular structure.

The positively charged headgroups prevent stable bola self-assembly at physiological conditions and the addition of siRNA neutralizes the charge and promotes self-assembly. Different bola/siRNA complexes were formulated through simple mixing and their morphologies were visualized by TEM. FIG. 17B-D shows that the size of the headgroup significantly changes the self-assembly behavior. With smaller headgroup, C18-G1 bolaamphiphiles can closely pack with each other and form nanofibers. The chirality of the headgroup also induces the twists into the fiber (see FIG. 17E) and the pitches could be observed in TEM (indicated by red arrows in FIG. 17B). As the headgroup size increases, both sterics and charge repulsion prevent highly ordered packing in nanofibers. C18-G2 forms single-layered vesicle with siRNA (see FIG. 17F), indicated by circular rings in TEM (see FIG. 17C). And C18-G3 could not form any ordered packing, with only dark micellar aggregates with no fine structure observed (see FIGS. 17D and 17G). In the dried TEM samples, size of vesicular complexes ranges from 50 nm to 100 nm in diameter, and micellar complexes 20-50 nm. In the dynamic light scattering (DLS) measurement, the average hydrodynamic diameter of vesicular complexes is ~150 nm and micellar aggregates ~100 nm.

The different self-assembly behavior could be confirmed by IR spectrum. Methylene $CH_2$ groups in the alkyl region prefers trans conformation in highly ordered packing structure, resulting in lower frequency of C—H stretch peaks. FIG. 12 shows that from G1 to G3 bola complexes, both the asymmetric (~2930 $cm^{-1}$) and symmetric (~2850 $cm^{-1}$) C—H stretch peaks shifted to higher frequency, indicating less ordered structure in the alkyl region. The decreased packing order agrees with the corresponding fiber, vesicle and micelle structure. The proposed different self-assembly could be further confirmed by the stability of different bola complexes. Anionic polymer dextran sulfate (DS) was added to pre-formed bola/siRNA complexes, and higher amount of DS required to break up the self-assembled structure and replace siRNA indicates higher stability. As shown in FIGS. 17J and 17L, bola-C18-G1, although has the lowest level of multivalency, exhibits strongest siRNA binding, with no siRNA release up to S/P of 30 (the molar ratio of sulfate from DS and phosphate from siRNA), while multivalent bola-C18-G2 and bola-C18-G3 show siRNA release at S/P of 23 and 15 respectively. Again such trend agrees with the stability of corresponding self-assembly structure.

A similar controllable self-assembly was also observed in bolas with fluorinated core (see FIG. 11). Vesicular structures with dark ring could be observed with bola-F10-G2 complexes (see FIG. 11F) and dark spherical aggregates observed with bola-F10-G3 (see FIG. 11G). Fibril structure was not observed in F10-G1 bolaamphiphiles (see FIG. 11E), possibly because the shorter hydrophobic core could not form highly ordered fiber structure. On the other hand, geometry of the hydrophobic core also influences the self-assembly. Bolas with a more linear core containing 1,4-trizaole ring could form monolayer vesicles with siRNA (see FIG. 11C), yet the kinked 1,5-triazole analog prevents effective packing and only micellar aggregates were observed (see FIG. 11D).

For the assembly of mono amphiphiphiles, both m-C11-G2 (see FIG. 11A) and m-OA-G2 (see FIG. 11B) complexes forms vesicles, possibly with a bilayer membrane, and fibril network was observed with the double tailed m-OA$_2$-G2 complex (see FIG. 11H). The proposed stability difference between mono and bola complexes could also be observed by DS competitive binding assay. m-C11-G2 and bola-C22-G2 have exactly the same amphiphilic composition, however, bola complexes exhibits much higher stability with little siRNA release up to S/P=30, while mono amphiphile complex starts to release siRNA at S/P=8 (see FIG. 13).

Determining Transfection Efficiency of Peptide Bolas by Cellular Uptake of siRNA.

FIG. 18A-D shows the fluorescence images of NIH 3T3 cells transfected with Cy3 labeled siRNA. Mono amphiphile was not able to delivery siRNA into the cells and no Cy3 fluorescence could be observed (see FIG. 18A). G1 bola forms aggregates attached to the cell surface, however, there large particles could not be internalized and no siRNA was observed inside the cytoplasm (see FIG. 18B). Both G2 and G3 bolas could delivery siRNA into the cells, with G2 exhibiting significantly higher efficiency (see FIGS. 18C and D).

The Cy3-siRNA uptake was then quantified by flow cytometry, with results summarized in see FIG. 18E-I. Compared with Lipofectamine, all three mono amphiphiles treated cells showed very low siRNA uptake (see FIG. 18E), while bolaamphiphiles bola-C18-G2 and bola-F10-G2 exhibited 20 to 40 times higher uptake than the control (see FIG. 18F). Bolas with either shorter alkane core (C6 and C12) or hydrophilic HEG core could not form stable complexes, and did not delivery Cy3-siRNA into the cells (see FIG. 18F). It is very interesting to note, that cell uptake was directly related to the morphologies of self-assembled complexes. Vesicular complexes formed by C18 and F10 G2 bolas exhibited much higher cell uptake than their G3 micellar complexes (see FIGS. 18G and 18H). Similarly, bolas containing 1,4-triazole core shows higher uptake than the 1,5-triazole analog (see FIG. 18I). The three graphs in FIG. 18G-I are plotted in different scale for better visualization, and among them, bola-F10-G2 transfected cells exhibited the highest siRNA uptake.

For better understanding the bioactivity of peptide bolas, bola-F10-G2 and bola-F10-G3 were chosen as representative vesicular and micellar aggregates to study the cell uptake pathway. FIG. 18J-L shows that the cell uptake of bola/Cy3-siRNA complexes are energy dependent, with low temperature completely blocking the uptake (see FIGS. 18J and 18K) and metabolic inhibitor NaN$_3$/2-deoxy-D-glucose inhibiting uptake in a concentration dependent manner (see FIG. 18L). Several pathways are involved for energy intensive active uptake, and small molecule inhibitors were used to specifically block three most common pathways: clathrin-mediated endocytosis (chlorpromazine), caveolar endocytosis (Genistein) and macropinocytosis (EIPA). As shown in FIGS. 18M and 18N, vesicular complexes (F10-G2) were internalized through both clathrin-mediated and caveolar pathways, while micellar complexes exclusively enters the cell through caveolar endocytosis. Dependency of the inhibitor concentration was also observed (see FIG. 15A-C), confirming the cellular uptake pathway.

The Gene Silencing of Peptide Bolas was Studied in an Engineered NIH 3T3 Cell Line with Green Fluorescence Protein (GFP) Expression.

Transfection efficiency was calculated by comparing the anti-GFP siRNA complexes treated cells with scrambled siRNA treated ones. FIGS. 19A and 19B summarizes the transfection results. Similarly to cell uptake studies, mono amphiphiles showed very low transfection efficiency, with only m-OA2-G2 inducing ~25% knockdown. Neither bolas with hydrophilic HEG core or fibril complexes formed by bola-C18-G1 was able to silence GFP expression, while both vesicular (bola-C18-G2, bola-F10-G2 and 1,4-TZ-G2) and micellar (bola-C18-G3, bola-F10-G3 and 1,5-TZ-G2) complexes both exhibited very high protein knockdown (~80%, see FIG. 19B). The reducible disulfide linker also helps transfection through facilitated siRNA release in cytoplasm, and a non-reducible linker (bola-C18-NR-G2) significantly reduces the transfection efficiency (~45%, see FIG. 19B).

Endosomal escape is a critical step for successful siRNA delivery, otherwise cargoes trapped in the endosome will be transported to lysosome and degraded by the hydrolytic enzymes. It has been found that histidine could help endosomal escape through a "proton sponge" effect or enhanced amphiphilicity under acidic conditions. As shown in FIG. 14, a vacuolar proton pump inhibitor, bafilomycin, significantly reduces the transfection efficiency of peptide bolas, confirming the critical role of histidine protonation in successful siRNA delivery.

Although micellar complexes showed much lower efficiency than vesicular complexes in cell uptake studies (see FIG. 18G-I), both were able to induce high level of GFP silencing under the 100 nM condition. However, upon reducing siRNA concentration, the difference in transfection efficiency became more obvious. Bola-F10-G2 remained effective as low as 25 nM siRNA concentration, while bola-F10-G3 showed almost linear dependency on siRNA concentration from 25 to 75 nM transfection (see FIG. 19C).

Lipofectamine also exhibited similar trend, with high level of silencing only achieved at higher siRNA concentration. The low effective dosage of bola-F10-G2-75H25W makes it a promising candidate for siRNA delivery application. Furthermore, the direct relationship from molecular structure to self-assembly behavior and subsequent biologic activity offers great opportunity to rationally design peptide bolaamphiphiles for different biomaterial application.

Aromatic Amino Acid Survey with Peptide Bolas.

A series of fluorocarbon bolaamphiphiles (bola-F10-G2) functionalized with 75% His and 25% aromatic amino acid were synthesized (see FIG. 20A) and screened for siRNA complexation and luciferase knockdown in MDA-MB-231 cells (see FIG. 20B). The aromatic amino acids were chosen based upon their commercial/synthetic availability with the FIG. 20C displaying a complete chart of the structures. One initial hypothesis tested was that N-methylation of Trp would result in a decrease in binding strength and transfection activity due to reduction in the intercalation potential. Gel-shift assays and transfection screening in Luc-MDA-MB-231 indeed indicated that the methylated Trp vector bound siRNA was much weaker and displayed comparatively poor transfection activity at lower N/P ratios and concentrations (see FIG. 20B). Similarly, O-methylation of Tyr had a similarly detrimental effect on both siRNA binding and knockdown effect (see FIG. 20B). Control vectors functionalized with 25% Leu or Val displayed no knockdown activity (see FIG. 20B). The importance of stereochemistry on transfection was examined by functionalizing bola-F10-G2 with a 75%/25% mixture of L-His/D-Trp. This compound was indistinguishable from the standard bola-F10-G2-HW vector in transfection and siRNA binding assays, suggesting that the cell uptake proceeds via an achiral (i.e. non-specific) mechanism. Another important result from the transfection screening was that the bolaamphiphile analog, in which the reducible disulfide linker was replaced with a short ethylene glycol segment (F10-PEG-G2-HW), displayed similar transfection activity in serum-free conditions, suggesting that GSH-triggered degradation is not important for the system. When the transfection was performed in high concentrations of serum; however, the disulfide vector greatly outperformed the one containing the PEG linker. This suggests that the more hydrophobic di-cysteamine linker results in a more stable vector/siRNA complex which is resistant to competition by serum proteins. Presumably the hydrophilic, flexible nature of the PEG linker leads to less stable co-assembled structures which are not stable in the presence of negatively-charged serum proteins.

Transfection screening of the artificial aromatic amino acid variants revealed that most derivatives displayed similar or attenuated transfection activity compared to the Trp and Tyr vectors. Addition of fluorine to the 4 or 5 position of the Trp or 3 position of Tyr reduced the efficacy of the resulting vectors, with $IC_{50}$ values reduced from ~3 nM for the unmodified vectors to 6-10 nM for the fluorinated analogs (see FIG. 20B). Multiple 4-Phe derivatives were screened with surprising results indicating that the 4-$NO_2$ analog was quite active while the 4-$NH_2$ failed to induce significant knockdown (see FIG. 20B). Previously it was shown that increasing the size of the aromatic ring (phenyl to napthyl) increased siRNA binding and transfection activity. Two modifications which had negative effects on transfection were 4-Br and 4-$CF_3$, presumably due to these groups interfering with intercalation and not contributing favorable hydrophobic or hydrogen bonding properties.

Effect on Peptide Bolas Colloidal Stability by PEGylation.

Although highly effective, siRNA complexes formed with the F10-G2-75H/25W vector have displayed significant aggregation over time, especially in buffers containing physiological relevant levels of salt (100 mM). In order to address the colloidal stability issue without redesign of the vector, co-formulation of the fluorocarbon bolaamphiphiles with PEG was investigated. First, synthesis of a fluorocarbon PEG (MW=2000) was accomplished with a one-pot reaction by activating a fluorinated alcohol with p-nitro chloroformate and subsequently reacting with a PEG-amine (See FIG. 21A). Next, a DLS assay was designed in order to mimic the transfection conditions and monitor aggregation of the complexes in high-salt buffer (see FIG. 21C). The complexes were first prepared in low-salt PBS (pH 7.4, 10 mM NaCl) and then diluted 5× into high-salt PBS (pH 7.4, 100 mM NaCl). DLS analysis was collected over 30 minutes, with any increase in size over time indicating a negative result. Under these conditions without PEGylation, the F10-G2-H/W complexes rapidly aggregate to form micron sized particles. Simply mixing fPEG and the vector in water prior to complexation with siRNA improved the colloidal stability, although 10 mol % fPEG was not sufficient to completely prevent aggregation. It was necessary to include 50 mol % fPEG in order to prevent aggregation, a level which negatively impacts transfection efficiency.

In order to ensure complete homogenization of the components before complexation, the fPEG and vector were dissolved in EtOH, the solvent removed to give a thin-film, and then the PEGylated vector dispersed in water. This strategy proved more effective than simple mixing with complete stabilization at 10 mol % fPEG. Transfection assays revealed that this formulation resulted in a slight decrease in knockdown efficacy (see FIG. 21B).

In summary, a direct link was found between the molecular structure of bolas to their self-assembly behavior and biological activity (see TABLE 1).

TABLE 1

| Molecular Structure | Self-Assembly | Cell Uptake | SiRNA Transfection |
|---|---|---|---|
| Mono amphiphile | Unstable liposome | Low, highly membrane disruptive | Low |
| Bola, longer core, small headgroup | Nanofiber | Aggregate around cell surface, no uptake | None |
| Bola, shorter core, medium headgroup | Monolayer vesicle | Clathrin- and caveolae-mediated endocytosis, high cell uptake | High Efficiency |
| Bola, large headgroup | Micellar Aggregates | Caveolae-mediated endocystosis, low cell uptake | Moderate Efficiency |

Summary of Peptide Amphiphile/Bolaamphile Structure-Property Relationships

Mono amphiphiles were found to form unstable assemblies with siRNA, and most complexes break apart before entering the cell, resulting in low cell uptake and transfection efficiency. Bolas with long core and small headgroup could form very stable fibril complexes with siRNA, however, such morphology could not be internalized by the cells. Bolas with medium headgroups were found to self-assemble into single-layered vesicles with siRNA, exhibiting high uptake and transfection efficiency. Large headgroups prevented ordered packing, therefore, such bolas complexes aggregate into random micelles, with moderate transfection efficiency. Further, colloidal stabilities of the bolas can be improved with PEGylation.

A number of embodiments have been described herein. Nevertheless, it will be understood that various modifications may be made without departing from the spirit and scope of this disclosure. Accordingly, other embodiments are within the scope of the following claims.

What is claimed is:

1. A compound comprising the formula:

$$D^1\text{-}(L^1)_x\text{-}C\text{-}(L^2)_y\text{-}D^2$$

wherein,
$D^1$ and $D^2$ are dendritic hydrophilic head groups comprising a plurality of branched peptides, wherein each head group comprises two to six generations of branching;
C is a linear hydrophobic core comprising an optionally substituted linear ($C_6$ to $C_{25}$)alkyl, an optionally substituted linear ($C_6$ to $C_{25}$)heteroalkyl, an optionally substituted linear ($C_6$ to $C_{25}$)alkenyl, an optionally substituted linear ($C_6$ to $C_{25}$)heteroalkenyl, an optionally substituted linear ($C_6$ to $C_{25}$)alkynyl, or an optionally substituted linear ($C_6$ to $C_{26}$)heteroalkynyl,
$L^1$ and $L^2$ are linkers which comprise a biodegradable group that is capable of being cleaved in the cytoplasm of a cell;
x is an integer selected from 0 to 5;
y is an integer selected from 0 to 5, and
wherein the compound contains only two dendritic hydrophilic head groups.

2. The compound of claim 1, wherein C has a structure of:

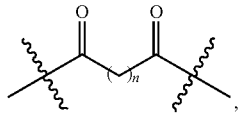

wherein,
n is an integer from 14 to 25.

3. The compound of claim 1, wherein C has the structure of:

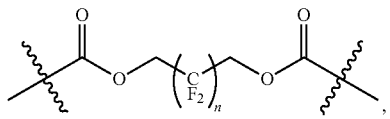

and
wherein n is an integer from 10 to 20.

4. The compound of claim 1, wherein $L^1$ and $L^2$ comprises a biodegradable bond selected from the group consisting of disulfide, ester, thioester, carbamate, amide, and thiocarbamate.

5. The compound of claim 4, wherein the $L^1$ and $L^2$ comprises the structure of:

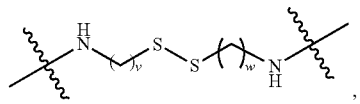

wherein,
v is an integer from 1 to 5; and
w is an integer from 1 to 5.

6. The compound of claim 1, wherein $D^1$ and/or $D^2$ comprise a plurality of linked D/L-arginine, D/L-lysine, D/L-aspartic acid, D/L-glutamic acid, D/L-serine, D/L-threonine, D/L-asparagine, D/L-glutamine, D/L-cysteine, D/L selenocysteine, D/L-alanine, D/L-isoleucine, D/L-leucine, D/L-methionine, D/L-valine residues, and/or any analog thereof, wherein D/L refers to the D-isomer or L-isomer of the amino acid.

7. The compound of claim 6, wherein $D^1$ and $D^2$ comprise a plurality of linked D/L-lysine residues.

8. The compound of claim 7, wherein $D^1$ and/or $D^2$ further comprise histidine residues.

9. The compound of claim 8, wherein $D^1$ and/or $D^2$ further comprise aromatic amino acid residues.

10. The compound of claim 9, wherein $D^1$ and $D^2$ comprise from 10 mol % to 90 mol % of histidine residues to 90 mol % to 10 mol % percent of aromatic amino acid residues.

11. The compound of claim 10, wherein $D^1$ and $D^2$ comprise from 25 mol % to 75 mol % of histidine residues to 75 mol % to 25 mol % percent of aromatic amino acid residues.

12. The compound of claim 9, wherein the aromatic amino acid residues are selected from:

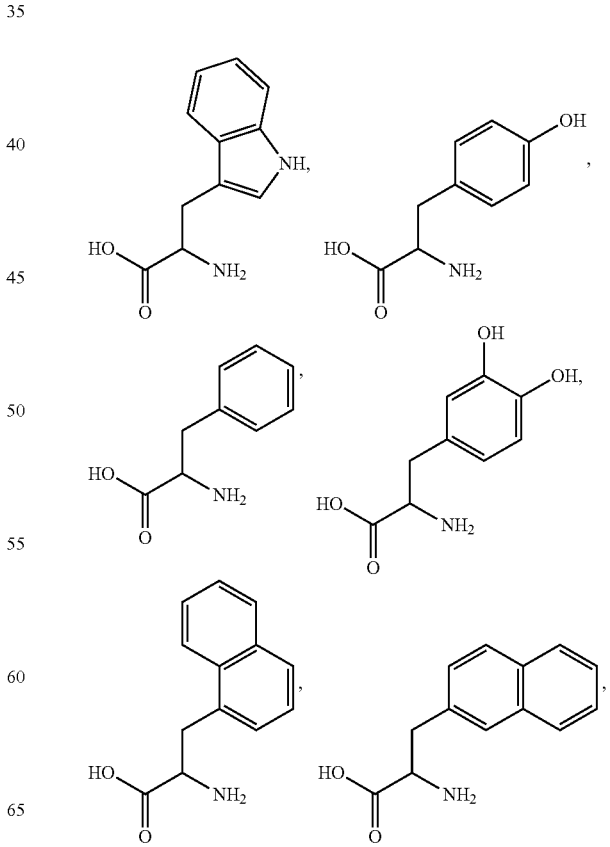

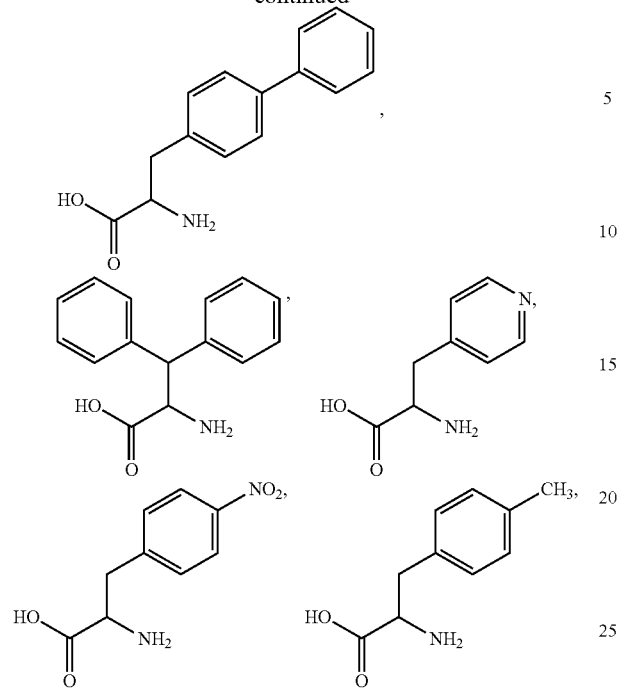
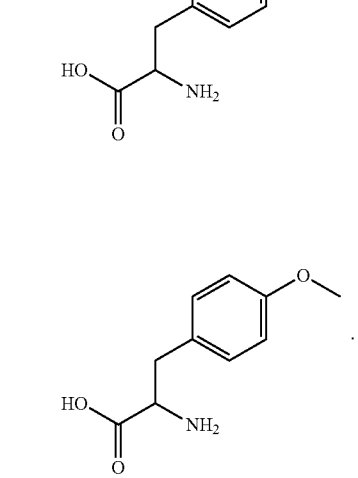
13. The compound of claim 1, wherein $D^1$ and $D^2$ comprise the structure of Formula I or Formula II:
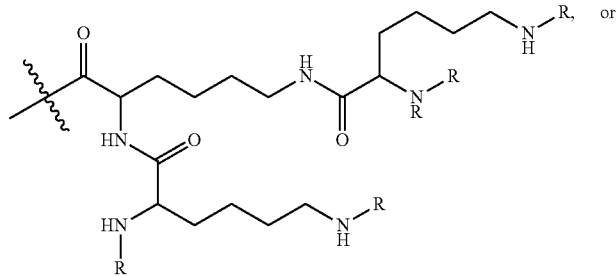
(Formula I)
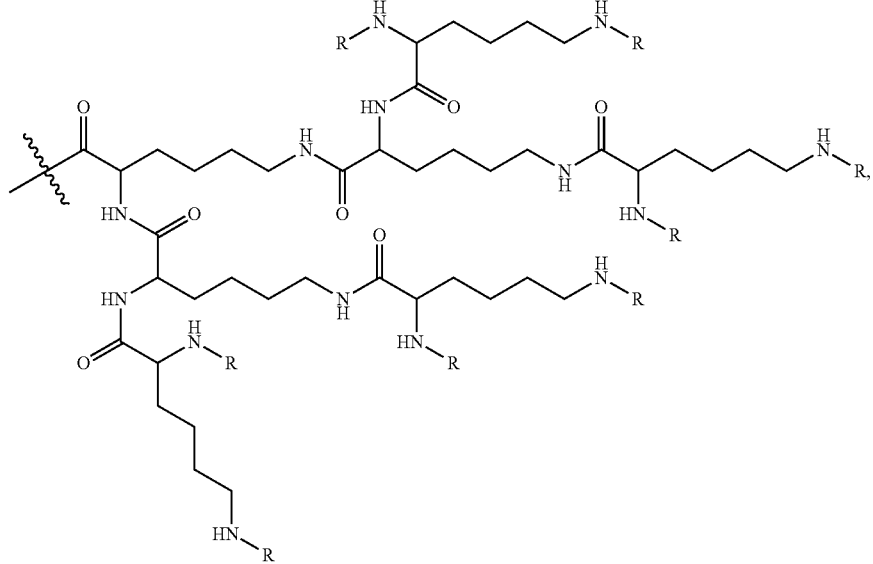
(Formula II)

wherein,
at least one of the R groups is a histidine residue and at least one of R groups is an aromatic amino acid residue.

14. The compound of claim 13, wherein for Formula I or Formula II, the R groups comprise 10 mol % to 90 mol % of histidine residues to 90 mol % to 10 mol % percent of aromatic amino acid residues.

15. The compound of claim 1, wherein the compound further comprises an encapsulated peptide, protein, nucleic acid, or drug.

16. The compound of claim 15, wherein the compound further comprises encapsulated nucleic acids.

17. The compound of claim 16, wherein the compound further comprises encapsulated siRNA.

18. A method of delivering a peptide, protein, nucleic acid, or drug across a cellular membrane into the interior of a cell, comprising:
contacting the cellular membrane with the compound of claim 15.

19. A method of delivering siRNA into the interior of a cell in vitro or in vivo comprising contacting the cell with the compound of claim 17.

20. A pharmaceutical composition comprising the compound of claim 15 and a pharmaceutically acceptable carrier.

21. A method of treating a disease or disorder in a subject comprising administering the pharmaceutical composition of claim 20, wherein the disease or disorder is selected from diabetes; cancer; infectious and parasitic diseases; inflammatory diseases; neurodegenerative diseases; autoimmune diseases; respiratory diseases; endocrine diseases eye diseases intestinal diseases; cardiovascular diseases idiopathic diseases; genetic disorders; growth disorders; congenital disorders: mental or behavioral disorders; adrenal disorders; thyroid disorders; calcium homeostasis disorders; pituitary gland disorders; and sex hormone disorders.

* * * * *